US006828473B2

(12) United States Patent
Burslem et al.

(10) Patent No.: US 6,828,473 B2
(45) Date of Patent: Dec. 7, 2004

(54) MODULATION OF PDE11A ACTIVITY

(75) Inventors: Martyn Frank Burslem, County of Kent (GB); Ian Dennis Harrow, County of Kent (GB); Jeremy Lanfear, County of Kent (GB); Stephen Charles Phillips, County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/040,570

(22) Filed: Nov. 1, 2001

(65) Prior Publication Data

US 2003/0061625 A1 Mar. 27, 2003

Related U.S. Application Data

(60) Provisional application No. 60/255,689, filed on Dec. 14, 2000, and provisional application No. 60/293,411, filed on May 24, 2001.

(30) Foreign Application Priority Data

Nov. 1, 2000 (GB) ............................................. 0026727
May 14, 2001 (GB) ............................................. 0111710

(51) Int. Cl.$^7$ ........................ A01K 67/027; C12N 5/00; C12N 5/02; C12N 5/06; C12N 5/10
(52) U.S. Cl. .......................... 800/18; 435/325; 435/354
(58) Field of Search ..................... 800/18, 14; 435/325, 435/354

(56) References Cited

U.S. PATENT DOCUMENTS 5,585,479 A * 12/1996 Hoke et al. ................. 436/24.5

FOREIGN PATENT DOCUMENTS

| EP | 0463756 | 6/1991 | ......... C07D/487/04 |
| EP | 0607439 | 9/1992 | ......... C07D/215/00 |
| EP | 0579496 | 7/1993 | ......... C07D/401/04 |
| WO | WO 9519978 | 7/1995 | ......... C07D/471/14 |
| WO | WO9728825 A | 8/1997 | |
| WO | WO 9902161 | 1/1999 | ......... A61K/31/52 |

OTHER PUBLICATIONS

Rossiter et al., 1989, Advances in Applied Biotechnology Series, pp. 57–69.*
Mullins, 1996, J. Clin. Invest., vol. 98, pp. S37–S40.*
Campbell and Wilmut, 1997, Theriogenology, vol. 47, pp. 63–72.*
McCreath, 2000, Nature, vol. 405, pp. 1066–1069.*
Kent–First, 2000, Nature Biotechnology, vol. 18, pp. 928–929.*
Dinnyes, 2002, Cloning and Stem Cells, vol. 4, pp. 81–90.*
Denning, 2001, Nature Biotechnology, vol. 19, pp. 559–562.*
Leonard, 1995, Immunological Reviews, vol. 148, pp. 97–114.*
Griffiths, 1998, Microscopy Research and Technique, vol. 41, pp. 344–358.*

Jin, S. et al, "Impaired growth and fertility of cAMP–specific phosphodiesterase PDE4D–deficient mice", Proceedings of the National Academy of Sciences of USA, vol. 96, No. 21, Oct. 12, 1999, pp. 11998–12003.

Fawcett, L., et al., *Molecular cloning and characterization of a distinct human phosphodiesterase gene family: PDE11A*; Proc. Natl. Acad. Sci.; USA, 2000; vol. 97; p. 3702–3707.

Hetman, J. M., et al., *Cloning and characterization of two splice variants of human phosphodiesterase 11A*, Proc. Natl. Acad. Sci.; USA, 2000; vol. 97; p. 12891–12895.

Baxendale, R., et al., *Human PDE11: a distinct, dual–substrate phosphodiesterase expressed in vascular smooth muscle and cardiac myocytes*; Circulation; 2000; 102(18):320.

Baxendale, R., et al., *Cellular localisation of phosphodiesterase type 11 (PDE11) in human corpus cavernosum and the contribution of PDE11 inhibition on nerve–stimulated relaxation*; J. Urology, 2001; 165(5); 223.

Baxendale, R., et al., *Phosphodiesterase type 11 (PDE11) cellular localisation: progress towards defining a physiological role in testis and/or reproduction*; J. Urology, 2001; 165(5); 340.

Yuasa, K., et al., *Isolation and characterization of two novel phosphodiesterase PDE11A variants showing unique structure and tissue–specific expression*; J. Biol. Chem., Oct. 6, 2000; 275(40):31469–79.

Yuasa, K., et al., *Genomic organization of the human phosphodiesterase PDE11A gene. Evolutionary relatedness with other PDEs containing GAF domains*, Eur. J. Biochem.; Jan. 2001; 268(1):168–78.

Yuasa, K., et al., *Identification of rat cyclic nucleotide phosphodiesterase 11A (PDE11A): comparison of rat and human PDE11A splicing variants*, Eur. J. Biochem.; Aug. 2001; 268(16):4440–8.

Kodama, K., et al., *Effects of a novel, selective and potent phosphodiesterase type V inhibitor, E4021, on myocardial ischemia in guinea pigs*, Euro. Journal of Pharm., vol. 263: 93–99, 1994.

(List continued on next page.)

Primary Examiner—Peter Paras
Assistant Examiner—Valarie Bertoglio
(74) Attorney, Agent, or Firm—Peter C. Richardson; Gregg C. Benson; Deborah A. Martin

(57) ABSTRACT

The invention provides genetically-modified non-human mammals and genetically-modified animal cells containing a functionally disrupted PDE11A gene. Also provided by the invention are methods of screening for agents that modulate PDE11A to modulate spermatogenesis, methods of treating mammals to modulate spermatogenesis, and methods of modulating cAMP and cGMP signal transduction in cells that express PDE11A.

3 Claims, 6 Drawing Sheets

OTHER PUBLICATIONS

Köhn, R., et al., *Relaxation of human ureteral smooth muscle in vitro by modulation of cyclic nucleotide–dependent pathways*, Urol Res, vol. 28: 110–115, 2000.

Lee, S., et al., *Discovery of potent cyclic GMP phosphodiesterase inhibitors, 2–pyridyl– and 2–imidazolyiquinazolines possessing cyclic GMP phosphodiesterase and thromboxane synthesis inhibitory activities*, J. Med. Chem., vol. 38: 3547–3557, 1995.

Middendorff, R., et al., *Multiple roles of the messenger molecule cGMP intesticular function*, Andrologia, vol. 32(1): 55–59, 2000.

Truss, M., et al., *Selective pharmacological manipulation of the smooth muscle tissue of the genitourinary tract: a glimpse into the future*, BJU International, vol. 83(2): 36–41, 1999.

* cited by examiner

Figure 2

P-11 SEQUENCES: Human cDNA, Mouse PCR product, Oligonucleotides

Fig. 2A  HUMAN P-11 SEQUENCE (partial cDNA, both strands shown):

(SEQ ID NO:1) 5'<AAGGCAGCCAACATCCCTCGTGCAGAACTGCCATCGATGACATTCATTTGATGACTTTCTCCGACGTTGATGCCATGATCACAGCTGCTCCGGATGTTCATGGAGCTGGGATGCTGGGGATGTACAGAAA>3'
(SEQ ID NO:2) 3'<TTCCGTCGGTTGTAGGGAGCACGTCTTGACGGTAGCTACTGTAAGTAAACTACTGAAAAGAGCTGCAACTACGGTACAGTAGTCGACGAGGCCTACAAGTACCTCGACCCTACCATGTCTTT>5'

(SEQ ID NO:3) Oligonucleotide 7744 (one strand):  5'<CTTCTGTACCATCCCAGCTCCATG>3'
(SEQ ID NO:4) Oligonucleotide 7745 (one strand):  5'<AAGGCAGCCAACATCCCTCTGGTGT>3'

→

PCR with oligonucleotides 7744 and 7745
using mouse genomic DNA as the template.

Fig. 2B  MOUSE P-11 SEQUENCE (PCR product, both strands shown; divergence from human seq. in lower case)

(SEQ ID NO:5) 5'<TCggAACTgGCCATCGATGACTCATTTCGATGACTTTCCTTGATGTTGATGCCATGATCACACGCGGTCTaCGGATGTT>3'
(SEQ ID NO:6) 3'<AGCCTTGACCGGTAGCTACTGTAGTGAAAGCTACTGAAAAGgAACTACAACTACGGTACTAGTGTCGgCGAGATGCCTACAA>5'

SEQUENCE LISTING

<160> NUMBER OF SEQ ID NOS: 8

<210> SEQ ID NO 1
<211> LENGTH: 132
<212> TYPE: DNA
<213> ORGANISM: Homo sapiens

<400> SEQUENCE: 1

```
aaggcagcca acatccctct ggtgtcagaa cttgccatcg atgacattca ttttgatgac      60
ttttctctcg acgttgatgc catgatcaca gctgctctcc ggatgttcat ggagctgggg     120
atggtacaga aa                                                         132
```

<210> SEQ ID NO 2
<211> LENGTH: 132
<212> TYPE: DNA
<213> ORGANISM: homo sapiens

<400> SEQUENCE: 2

```
ttccgtcggt tgtagggaga ccacagtctt gaacggtagc tactgtaagt aaaactactg      60
aaaagagagc tgcaactacg gtactagtgt cgacgagagg cctacaagta cctcgacccc     120
taccatgtct tt                                                         132
```

<210> SEQ ID NO 3
<211> LENGTH: 25
<212> TYPE: DNA
<213> ORGANISM: homo sapiens

```
<400> SEQUENCE: 3
tttctgtacc atccccagct ccatg                                    25

<210> SEQ ID NO 4
<211> LENGTH: 25
<212> TYPE: DNA
<213> ORGANISM: homo sapiens

<400> SEQUENCE: 4
aaggcagcca acatccctct ggtgt                                    25

<210> SEQ ID NO 5
<211> LENGTH: 83
<212> TYPE: DNA
<213> ORGANISM: mus musculus

<400> SEQUENCE: 5
tcggaactgg ccatcgatga catccatttc gatgactttt cccttgatgt tgatgccatg    60
atcacagccg ctctacggat gtt                                     83

<210> SEQ ID NO 6
<211> LENGTH: 83
<212> TYPE: DNA
<213> ORGANISM: mus musculus

<400> SEQUENCE: 6
agccttgacc ggtagctact gtaggtaaag ctactgaaaa gggaactaca actacggtac    60
tagtgtcggc gagatgccta caa                                     83

<210> SEQ ID NO 7
<211> LENGTH: 10
<212> TYPE: DNA
<213> ORGANISM: Mus musculus

<400> SEQUENCE: 7
atgacattca                                                    10

<210> SEQ ID NO 8
<211> LENGTH: 10
<212> TYPE: DNA
<213> ORGANISM: Mus musculus

<400> SEQUENCE: 8
ctcgacgttg                                                    10
```

MODULATION OF PDE11A ACTIVITY

This application claims priority, under 35 U.S.C. § 119(e), from U.S. provisional application 60/255,689, filed Dec. 14, 2000, and from U.S. provisional application 60/293,411 filed May 24, 2001.

FIELD OF THE INVENTION

The present invention relates to genetically-modified non-human mammals and genetically-modified animal cells containing a functionally disrupted PDE11A gene. The invention also features methods of screening for agents that modulate PDE11A and methods of modulating cAMP and cGMP signal transduction in cells that express PDE11A.

BACKGROUND OF THE INVENTION

Cyclic nucleotide phosphodiesterases (PDEs) catalyze the hydrolysis of cyclic nucleotides, such as the second messengers cAMP (cyclic adenosine 3'5'-monophosphate) and cGMP (cyclic guanine 3'5'-monophosphate). Thus, PDEs play a pivotal regulatory role in a wide variety of signal transduction pathways (Beavo, Physiol. Rev. 75: 725–48, 1995). For example, PDEs mediate processes involved in vision (McLaughlin et al., Nat. Genet. 4: 130–34, 1993), olfaction (Yan et al., Proc. Natl. Acad. Sci. USA 92: 9677–81, 1995), platelet aggregation (Dickinson et al. Biochem. J. 323: 371–77, 1997), aldosterone synthesis (MacFarland et al., J. Biol. Chem. 266: 136–42, 1991), insulin secretion (Zhao et al., J. Clin. Invest. 102: 869–73, 1998), T cell activation (Li et al., Science 283: 848–51, 1999), and smooth muscle relaxation (Boolell et al., Int. J. Impot. Res. 8: 47–52, 1996; Ballard et al., J. Urol. 159: 2164–71, 1998).

PDEs form a superfamily of enzymes that are subdivided into 11 major families (Beavo, Physiol. Rev. 75: 725–48, 1995; Beavo et al., Mol. Pharmacol. 46: 399–05, 1994; Soderling et al., Proc. Natl. Acad. Sci. USA 95: 8991–96, 1998; Fisher et al., Biochem. Biophys. Res. Commun. 246: 570–77, 1998; Hayashi et al., Biochem. Biophys. Res. Commun. 250: 751–56, 1998; Soderling et al., J. Biol. Chem. 273: 15553–58, 1998; Fisher et al., J. Biol. Chem. 273: 15559–64, 1998; Soderling et al., Proc. Natl. Acad. Sci. USA 96: 7071–76, 1999; and Fawcett et al., Proc. Natl. Acad. Sci. USA 97: 3702–07, 2000).

Each PDE family is distinguished functionally by unique enzymatic characteristics and pharmacological profiles. In addition, each family exhibits distinct tissue, cell, and subcellular expression patterns (Beavo et al., Mol. Pharmacol. 46: 399–405, 1994; Soderling et al., Proc. Natl. Acad. Sci. USA 95: 8991–96, 1998; Fisher et al., Biochem. Biophys. Res. Commun. 246: 570–77, 1998; Hayashi et al., Biochem. Biophys. Res. Commun. 250: 751–56, 1998; Soderling et al., J. Biol. Chem. 273: 15553–58, 1998; Fisher et al., J. Biol. Chem. 273: 15559–64, 1998; Soderling et al., Proc. Natl. Acad. Sci. USA 96: 7071–76, 1999; Fawcett et al., Proc. Natl. Acad. Sci. USA 97: 3702–07, 2000; Boolell et al., Int. J. Impot. Res. 8: 47–52, 1996; Ballard et al., J. Urol. 159: 2164–71, 1998; Houslay, Semin. Cell Dev. Biol. 9: 161–67, 1998; and Torphy et al., Pulm. Pharmacol. Ther. 12: 131–35, 1999). Therefore, by administering a compound that selectively regulates the activity of one family or subfamily of PDE enzymes, it is possible to regulate cAMP and/or cGMP signal transduction pathways in a cell- or tissue-specific manner.

PDE11 is one of the most recently described families of PDEs; PDE11A is the sole member of this family so far identified (Fawcett et al., Proc. Natl. Acad. Sci. USA 97: 3702–07, 2000, hereinafter "Fawcett, 2000," Yuasa et al., J. Biol. Chem. 275: 31469–79, 2000, hereinafter "Yuasa, 2000"). While PDE11A is known to be expressed in, e.g., testis, skeletal muscle, kidney, liver, various glandular tissue (e.g., pituitary, salivary, adrenal, mammary, and thyroid), pancreas, spinal cord, and trachea (Fawcett, 2000), little is known about PDE11A function. The present invention provides biological tools to study PDE11A function and methods to identify agents that regulate PDE11A activity for use in treating diseases and conditions that are linked to these PDE11A functions.

One embodiment of the present invention is the provision of a PDE11A knockout mouse, which provides an excellent opportunity to investigate genes involved in, inter alia, spermatogenesis, and, when compared with the wildtype mouse, to dissect out the components involved in spermatogenesis. One method for this type of analysis is microarray technology. With DNA microarray technology, it becomes possible to monitor large-scale gene expression over time. Prefabricated arrays of large numbers of especially designed oligonucleotide probes, e.g. as manufactured by Affymetrix (CA, USA), enable simultaneous hybridization-based analysis of thousands of genes.

SUMMARY OF THE INVENTION

The present invention features genetically-modified animal cells and genetically-modified non-human mammals containing a disrupted PDE11A gene, as well as assays for identifying PDE11A function in cells and tissues that express PDE11A, methods for identifying agents that modulate these PDE11A functions, and methods of treating or preventing diseases or conditions in mammals by modulating PDE11A function. For example, modulators of PDE11A activity are administered to a mammal to modulate spermatogenesis.

One aspect of the invention features a genetically-modified, non-human mammal, wherein the modification results in a functionally disrupted PDE11A gene. Preferably, the mammal is heterozygous for the modification. More preferably, the mammal is homozygous for the modification. In other preferred embodiments, the mammal is a rodent, more preferably, a mouse.

In a second aspect, the invention provides a genetically-modified animal cell, wherein the modification comprises a functionally disrupted PDE11A gene. Preferably, the animal cell is heterozygous for the modification. More preferably, the cell is homozygous for the modification. In other preferred embodiments, the cell is an embryonic stem (ES) cell, and/or the cell is human or murine.

The third aspect of the invention features a method of identifying an agent that modulates spermatogenesis, involving contacting an agent with a PDE11A polypeptide and measuring PDE11A activity, wherein a difference between the activity in the absence of the agent and in the presence of the agent is indicative that the agent can modulate spermatogenesis. Preferably, the method identifies an agent that inhibits PDE11A activity for use in decreasing spermatogenesis.

In a related fourth aspect, the invention also provides a method of identifying an agent that modulates spermatogenesis, which includes contacting an agent with a cell that expresses a PDE11A polypeptide and measuring PDE11A activity or PDE11A expression, wherein a difference between the activity or expression in the absence of the agent and in the presence of the agent is indicative that the agent can modulate spermatogenesis.

The fifth aspect provides a method of modulating spermatogenesis in a mammal, the method comprising administering an agent that modulates PDE11A activity. Preferably, the agent administered reduces PDE11A activity and reduces spermatogenesis.

Featured in the sixth aspect is a method of modulating cAMP and/or cGMP-mediated signal transduction in a mammal in testis, prostate, pituitary gland, bladder urothelium and/or bladder nerve fibers, neurons, skeletal muscle, cardiac myocytes, vascular smooth muscle, and/or vascular endothelial cells, which includes administering an agent that modulates PDE11A activity. In preferred embodiments, the agent selective for PDE11A, or is UK-336,017 (IC-351), UK-227,786 (E4021), or UK-235,187.

The invention also features in a seventh aspect, a method of treating hypertension, cardiac insufficiency, atherosclerosis, hyperprolactinemia, growth hormone insufficiency, incontinence, or disorders associated with skeletal muscle metabolism or contractility, wherein the method comprises administering an agent that modulates PDE11A activity. Preferably, the agent is selective for PDE11A. More preferably, the agent is UK-336,017 (IC-351), UK-227,786 (E4021), or UK-235,187.

In an eighth aspect, the invention provides biomarkers indicative of modulated spermatogenesis in a mammal; these biomarkers can be used to monitor spermatogenesis in a mammal as well as for monitoring diseases or disorders characterised by reduced spermatogenesis. These biomarkers are useful in the clinical assessment of spermatogenesis, and can be used to aid in the selection of the appropriate therapeutic intervention. The biomarkers of the present invention are selected from the group consisting of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 and Krox-24 binding protein.

In a related ninth aspect, the invention provides biomarkers indicative of modulated cAMP and/or cGMP-mediated signal transduction in a mammal in testis, prostate, pituitary gland, bladder urothelium and/or bladder nerve fibers, neurons, skeletal muscle, cardiac myocytes, vascular smooth muscle, and/or vascular endothelial cells.

In a tenth aspect of the present invention, there is provided a method of modulating spermatogenesis in a mammal, said method comprising administering a modulator of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein.

In a related eleventh aspect, the invention provides a method of modulating cAMP and/or cGMP-mediated signal transduction in a mammal in testis, prostate, pituitary gland, bladder urothelium and/or bladder nerve fibers, neurons, skeletal muscle, cardiac myocytes, vascular smooth muscle, and/or vascular endothelial cells, said method comprising administering a modulator of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein.

Preferably, said modulator of the tenth and eleventh aspects of the invention is an inhibitor or antagonist of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein. More preferably, said inhibitor or antagonist is an antisense oligonucleotide or ribozyme against, or a compound that down-regulates the transcription and/or translation of, any gene(s) which encode(s) any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein.

In a preferred embodiment of the invention, if a male contraceptive agent is desired (i.e. to reduce spermatogenesis), then said agent will comprise an inhibitor or antagonist of any one or more Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen or HR6A. Such an agent will essentially have the effect of decreasing the presence in the testis of any one or more Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen or HR6A.

In another preferred embodiment of the invention, if a male pro-fertility agent is desired (i.e. to increase or normalize spermatogenesis), then said agent will comprise an inhibitor or antagonist of any one or more Protamine 1, sp32, mCDC46, Adenylate kinase 2, AKAP121 or Krox-24 binding protein. Such an agent will essentially have the effect of decreasing the presence in the testis of any one or more Protamine 1, sp32, mCDC46, Adenylate kinase 2, AKAP121 or Krox-24 binding protein. The term "normalize" is used in the present context to denote an increase in spermatogenesis, where the starting base level of spermatogenesis is below normal levels. This compares to the use of the term "increase", which is used in the present context to denote an increase in spermatogenesis, where the starting base level of spermatogenesis is already at a normal level.

Alternatively, said modulator of the tenth and eleventh aspects of the invention is a stimulator, activator or agonist of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein. Preferably, said stimulator or activator is a stimulator or activator of the transcription and/or translation of any gene(s) which encode(s) any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein.

In a preferred embodiment of the invention, if a male contraceptive agent is desired (i.e. to reduce spermatogenesis), then said agent will comprise a stimulator, activator or agonist of any one or more Protamine 1, sp32, mCDC46, Adenylate kinase 2, AKAP121 or Krox-24 binding protein. Such an agent will essentially have the effect of increasing the presence in the testis of any one or more Protamine 1, sp32, mCDC46, Adenylate kinase 2, AKAP121 or Krox-24 binding protein.

In another preferred embodiment of the invention, if a male pro-fertility agent is desired (i.e. to increase or normalize spermatogenesis), then said agent will comprise a stimulator, activator or agonist of any one or more Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, or HR6A. Such an agent will essentially have the effect of increasing or normalizing the presence in the testis of any one or more Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen or HR6A. The term "normalize" is used in the present context to denote an increase in spermatogenesis, where the starting base level of spermatogenesis is below normal levels. This compares to the use of the term "increase", which is used in the present context to denote an increase in spermatogenesis, where the starting base level of spermatogenesis is already at a normal level.

According to a twelfth aspect of the invention, there is provided use of a modulator of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein, in the manufacture of a medicament for modulating spermatogenesis in a mammal.

According to a thirteenth aspect of the invention, there is provided use of a modulator of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein, in the manufacture of a medicament for modulating cAMP and/or cGMP-mediated signal transduction in a mammal in testis, prostate, pituitary gland, bladder urothelium and/or bladder nerve fibers, neurons, skeletal muscle, cardiac myocytes, vascular smooth muscle, and/or vascular endothelial cells.

Preferably, said modulator of the twelfth and thirteenth aspects of the invention is an inhibitor or antagonist of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein. More preferably, said inhibitor or antagonist is an antisense oligonucleotide or ribozyme against, or a compound that down-regulates the transcription and/or translation of, any gene(s) which encode(s) any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein.

Alternatively, said modulator of the twelfth and thirteenth aspects of the invention is a stimulator, activator or agonist of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein. More preferably, said stimulator or activator is a stimulator or activator of the transcription and/or translation of any gene(s) which encode(s) any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein.

It will be appreciated that the inhibitors or antagonists of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein can be compounds that reduce the activity of the target, antibodies specific for the target, as well as antisense oligonucleotides or ribozymes or transcription inhibitors which have the effect of reducing the amount of the target produced. It will also be appreciated that stimulators, activators or agonists of any one or more of Corticosteroid binding globulin, Centrin 3, XRCC1, Chromobox M33, GABA-A (gamma 3 sub-unit), Prohormone convertase 5, Leydig Insulin-like peptide, Calpain 3, Y-Box 3, Chromogranin B, Cryptdin I, PP2B, Glutamate cysteine ligase, Nidogen, HR6A, Protamine 1, sp32, mCDC46, Adenylate kinase 2, AKAP121 or Krox-24 binding protein can comprise compounds that increase the activity of the target itself, as well as compounds that increase the expression of the target; another way to achieve increased activity of the target is to deliver the target itself, either as protein or its coding region in an appropriate vector as gene therapy.

According to a fourteenth aspect of the invention, there is provided use of agent that modulates PDE11A activity in the manufacture of a medicament for the modulation of spermatogenesis. Preferably, said agent reduces PDE11A activity and said modulation is reduction of spermatogenesis.

According to a fifteenth aspect of the invention, there is provided use of an agent that modulates PDE11A activity in the manufacture of a medicament for the modulation of cAMP and/or cGMP-mediated signal transduction in a mammal in testis, prostate, pituitary gland, bladder urothelium and/or bladder nerve fibers, neurons, skeletal muscle, cardiac myocytes, vascular smooth muscle, and/or vascular endothelial cells.

According to a sixteenth aspect of the invention, there is provided use of an agent that modulates PDE11A activity in the manufacture of a medicament for the treatment of hypertension, cardiac insufficiency, atherosclerosis, hyperprolactinemia, growth hormone insufficiency, incontinence, or disorders associated with skeletal muscle metabolism or contractility.

Preferably, the agent of the fourteenth, fifteenth and sixteenth aspects of the present invention is UK-336,017 (IC-351), UK-227,786 (E4021), or UK-235,187.

It will be appreciated that the present invention provides that the modulation of the PDE11A activity can be either a reduction in PDE11A activity, leading to, inter alia, a reduction in spermatogenesis, or an increase in PDE11A activity, leading to, inter alia, an increase in or normalization of spermatogenesis. Agents of the invention that result in a reduction in spermatogenesis can be classed as male contraceptive agents. Agents of the invention that result in an increase in or normalization of spermatogenesis can be classed as male pro-fertility agents.

Those skilled in the art will fully understand the terms used herein in the description and the appendant claims to describe the present invention. Nonetheless, unless otherwise provided herein, the following terms are as described immediately below.

By "coding sequence" or "coding region" is meant a nucleic acid molecule having sequence information necessary to produce a gene product when the sequence is expressed.

By "antisense oligonucleotide" is meant a small nucleic acid molecule, typically between about 10 to 50 nucleotides long, which may be unmodified RNA or DNA or modified RNA or DNA; it is designed to hybridize to the respective transcript, and thereby reduce its translation into protein, e.g. by blocking translation or by facilitating rapid degradation of the respective transcript.

By "ribozyme" is meant a nucleic acid molecule, which can be unmodified RNA or DNA or modified RNA or DNA, which is designed to hybridize and cleave the respective transcript.

The term "antibody" as used herein includes polyclonal and monoclonal antibodies, single chain, chimeric and humanized antibodies, as well as antibody fragments, whether produced by recombinant or proteolytic means. The term is also meant to include the products of any antibody-derived expression libraries, e.g. single-chain Fv or Fab fragment expression libraries.

By "biomarker" or "marker" is meant any molecule, e.g. a transcript of a gene or the translation product thereof, which is indicative of a condition, disorder, disease or dysfunction, or the status in the progression of a process, e.g. spermatogenesis, or the status in the progression of a condition, disorder, disease or dysfunction. For example, a particular gene may be down-regulated (reduced expression) in a particular disease. In such a disease, therefore, transcripts or translation products of the particular gene will be less abundant than the same transcripts or translation products in a non-diseased individual. Thus, since the abundance of particular transcripts or translation products may be ascertained using, for example, microarray technology, the particular gene (or rather its transcripts or translation products) will act as a marker ("biomarker") of the disease/progression of the disease (reduced abundance of transcripts or translation products will be highly indicative of the disease state). Similarly, a particular gene may be up-regulated (increased expression) in a particular disease. In such a disease, therefore, transcripts or translation products of the particular gene will be more abundant than the same transcripts or translation products in a non-diseased individual. Thus, since the abundance of particular transcripts or translation products may be ascertained using, for example, microarray technology, the particular gene (or rather its transcripts or translation products) will act as a marker ("biomarker") of the disease/progression of the disease (increased abundance of transcripts or translation products will be highly indicative of the disease state).

The use of differential gene expression as biomarkers is described in, for example, Molecular Classification of Cancer: Class Discovery and Class Prediction by Gene Expression Monitoring. T. R. Golub, D. K. Slonim, P. Tamayo, C. Huard, M. Gaasenbeek, J. P. Mesirov, H. Coller, M. L. Loh, J. R. Downing, M. A. Caligiuri, C. D. Bloomfield, and E. S. Lander. Science, 286: 531–537 (1999), and Delineation of Prognostic Biomarkers in Prostate Cancer. Dhanasekaran S M, Barrette T R, Ghosh D, Shah R, Varambally S, Kurachi K, Pienta K J, Rubin M A, Chinnaiyan A M. Nature, 412: 822–825 (2001), both of which are incorporated herein by reference.

"Microarray technology" or "DNA microarray technology" is now state of the art. The use of such technology in the analysis of differential gene expression is described in, for example, Discovery and analysis of inflammatory disease-related genes using cDNA microarrays. R. Heller et al. Proc. Natl. Acad. Sci (USA), 94: 2150–2155 (1997), Quantitative Monitoring of Gene Expression Patterns with a Complimentary DNA Microarray. M. Schena et al., Science, 270: 467–470 (1995), and Expression monitoring by hybridisation to high-density oligonucleotide arrays. D. J. Lockhart et al., Nature Biotechnology, 14: 1675–1680 (1996), all of which are incorporated herein by reference.

A non-human mammal or an animal cell that is "genetically-modified" is heterozygous or homozygous for a modification that is introduced into the non-human mammal or animal cell, or into a progenitor non-human mammal or animal cell, by genetic engineering. The standard methods of genetic engineering that are available for introducing the modification include homologous recombination, viral vector gene trapping, irradiation, chemical mutagenesis, and the transgenic expression of a nucleotide sequence encoding antisense RNA alone or in combination with catalytic ribozymes. Preferred methods for genetic modification are those which modify an endogenous gene by inserting a "foreign nucleic acid sequence" into the gene locus, e.g., by homologous recombination or viral vector gene trapping. A "foreign nucleic acid sequence" is an exogenous sequence that is non-naturally occurring in the gene. This insertion of foreign DNA can occur within any region of the PDE11A gene, e.g., in an enhancer, promoter, regulator region, non-coding region, coding region, intron, or exon. The most preferred method of genetic engineering is homologous recombination, in which the foreign nucleic acid sequence is inserted in a targeted manner either alone or in combination with a deletion of a portion of the endogenous gene sequence.

By a PDE11A gene that is "functionally disrupted" is meant a PDE11A gene that is genetically modified such that the cellular activity of the PDE11A polypeptide encoded by the disrupted gene is decreased in cells that normally express a wild type version of the PDE11A gene. When the genetic modification effectively eliminates all wild type copies of the PDE11A gene in a cell (e.g., the genetically-modified, non-human mammal or animal cell is homozygous for the PDE11A gene disruption or the only wild type copy of PDE11A gene originally present is now disrupted), then the genetic modification results in a reduction in PDE11A polypeptide activity as compared to an appropriate control cell that expresses the wild type PDE11A gene. This reduction in PDE11A polypeptide activity results from either reduced PDE11A gene expression (i.e., PDE11A mRNA levels are effectively reduced and produce reduced levels of PDE11A polypeptide) and/or because the disrupted PDE11A gene encodes a mutated polypeptide with reduced function or stability as compared to a wild type PDE11A polypeptide. Preferably, the activity of PDE11A polypeptide in the genetically-modified, non-human mammal or animal cell is reduced to 50% or less of wild type levels, more preferably, to 25% or less, and, even more preferably, to 10% or less of wild type levels. Most preferably, the PDE11A gene disruption results in non-detectable PDE11A activity.

By a "genetically-modified, non-human mammal" containing a functionally disrupted PDE11A gene is meant a non-human mammal that is originally produced, for example, by creating a blastocyst or embryo carrying the desired genetic modification and then implanting the blastocyst or embryo in a foster mother for in utero development. The genetically-modified blastocyst or embryo can be made, in the case of mice, by implanting a genetically-modified embryonic stem (ES) cell into a mouse blastocyst or by aggregating ES cells with tetraploid embryos. Alternatively, various species of genetically-modified embryos can be obtained by nuclear transfer. In the case of nuclear transfer, the donor cell is a somatic cell or a pluripotent stem cell, and it is engineered to contain the desired genetic modification that functionally disrupts the PDE11A gene. The nucleus of this cell is then transferred into a fertilized or parthenogenetic oocyte that is enucleated; the embryo is reconstituted, and developed into a blastocyst. A genetically-modified blastocyst produced by either of the above methods is then implanted into a foster mother according to standard methods well known to those skilled in the art. A "genetically-modified, non-human mammal" includes all progeny of the mammals created by the methods described above, provided that the progeny inherit at least one copy of the genetic modification that functionally disrupts the PDE11A gene. It is preferred that all somatic cells and germline cells of the genetically-modified mammal contain the modification. Preferred non-human animals that are genetically-modified to contain a disrupted PDE11A gene include rodents, such as mice and rats, cats, dogs, rabbits, guinea pigs, hamsters, sheep, pigs, and ferrets.

By a "genetically-modified animal cell" containing a functionally disrupted PDE11A gene is meant an animal cell, including a human cell, created by genetic engineering to contain a functionally disrupted PDE11A gene, as well as daughter cells that inherit the disrupted PDE11A gene. These cells may be genetically-modified in culture according to any standard method known in the art. As an alternative to genetically modifying the cells in culture, non-human mammalian cells may also be isolated from a genetically-modified, non-human mammal that contains a PDE11A gene disruption. The animal cells of the invention may be obtained from primary cell or tissue preparations as well as culture-adapted, tumorigenic, or transformed cell lines. These cells and cell lines are derived, for example, from endothelial cells, epithelial cells, islets, neurons and other neural tissue-derived cells, mesothelial cells, osteocytes, lymphocytes, chondrocytes, hematopoietic cells, immune cells, cells of the major glands or organs (e.g., testicle, liver, lung, heart, stomach, pancreas, kidney, and skin), muscle cells (including cells from skeletal muscle, smooth muscle, and cardiac muscle), exocrine or endocrine cells, fibroblasts, and embryonic and other totipotent or pluripotent stem cells (e.g., ES cells, ES-like cells, and embryonic germline (EG) cells, and other stem cells, such as progenitor cells and tissue-derived stem cells). The preferred genetically-modified cells are ES cells, more preferably, mouse or rat ES cells, and, most preferably, human ES cells.

By an "ES cell" or an "ES-like cell" is meant a pluripotent stem cell derived from an embryo, from a primordial germ cell, or from a teratocarcinoma, that is capable of indefinite self renewal as well as differentiation into cell types that are representative of all three embryonic germ layers.

By a "PDE11A gene" is meant the nucleic acid sequences encoding the polypeptides disclosed in Fawcett, 2000, (human PDE11A1, GenBank Accession No. AJ251509), WO 00/40733 (human PDE11A1 and PDE11A2), or Yuasa, 2000 (human PDE11A3 and PE11A4, GenBank Accession No. AB036704 and AB038041), as well as any human allelic variants and any mammalian sequences encoding homologues having PDE11A activity and their allelic variants. By a "PDE11 polypeptide" is meant the phosphodiesterases disclosed in Fawcett, 2000 or Yuasa, 2000, as well as any polypeptides encoded by any human allelic variants and any mammalian homologues having PDE11A activity. As used herein, the term "homologue" means a protein that is evolutionarily related to and shares substantial structural and functional similarity with a reference protein in a different species (e.g., human and mouse PDE11A polypeptides).

By "PDE11A polypeptide activity" or "PDE11A polypeptide-like activity" or "PDE11A activity" is meant the hydrolysis of cAMP or cGMP by a polypeptide encoded by a PDE11A gene. Such activity in a cell can be modulated at the level of PDE11A expression (e.g., by changing the amount of polypeptide that is effectively present within a cell) or by modifying the particular functional characteristics of each PDE11A polypeptide molecule (e.g., by changing the $K_m$ of hydrolysis for the mutated polypeptide).

By "modulates" is meant increases or decreases (including a complete elimination).

By an agent that is "selective" for modulating PDE11A activity is meant an agent that primarily effects PDE11A while producing little effect on another PDE at the same concentration of agent. For example, if an agent is selective for inhibiting PDE11A, the IC50 of the agent for PDE11A is at least 20 fold, more preferably, at least 30 fold, even more preferably, at least 50 fold, and, even more preferably, at least 100 fold, lower in concentration as compared to the IC50 for one or more PDEs from the group of PDEs 1–10. Preferably, the agent is selective for PDE11A as compared to PDE7–10, and, even more preferably, as compared to all of PDEs 1–10, especially PDE3–6.

Other features and advantages of the invention will be apparent from the following detailed description and from the claims. While the invention is described in connection with specific embodiments, it will be understood that other changes and modifications that may be practiced are also part of this invention and are also within the scope of the appendant claims. This application is intended to cover any equivalents, variations, uses, or adaptations of the invention that follow, in general, the principles of the invention, including departures from the present disclosure that come within known or customary practice within the art, and that are able to be ascertained without undue experimentation. Additional guidance with respect to making and using nucleic acids and polypeptides is found in standard textbooks of molecular biology, protein science, and immunology (see, e.g., Davis et al., Basic Methods in Molecular Biology, Elsevir Sciences Publishing, Inc., New York, N.Y., 1986; Hames et al., Nucleic Acid Hybridization, IL Press, 1985; Molecular Cloning, Sambrook et al., Current Protocols in Molecular Biology, Eds. Ausubel et al., John Wiley and Sons; Current Protocols in Human Genetics, Eds. Dracopoli et al., John Wiley and Sons; Current Protocols in Protein Science, Eds. John E. Coligan et al., John Wiley and Sons; and Current Protocols in Immunology, Eds. John E. Coligan et al., John Wiley and Sons). All publications mentioned herein are incorporated by reference in their entireties.

DESCRIPTION OF THE FIGURES

FIG. 2A shows an exemplary human PDE11A sequence (SEQ ID NOS: 1 and 2) used to generate PCR primers (SEQ ID NOS: 3 and 4) for use in obtaining the corresponding murine gene sequence by PCR amplification.

FIG. 2B shows the murine PDE11A gene PCR product generated using the primers shown in FIG. 2A. These sequences are examples of murine PDE11A sequences that can be used to design the homology arms of a PDE11A targeting construct, as shown in FIG. 1.

DETAILED DESCRIPTION OF THE INVENTION

Figure 1:
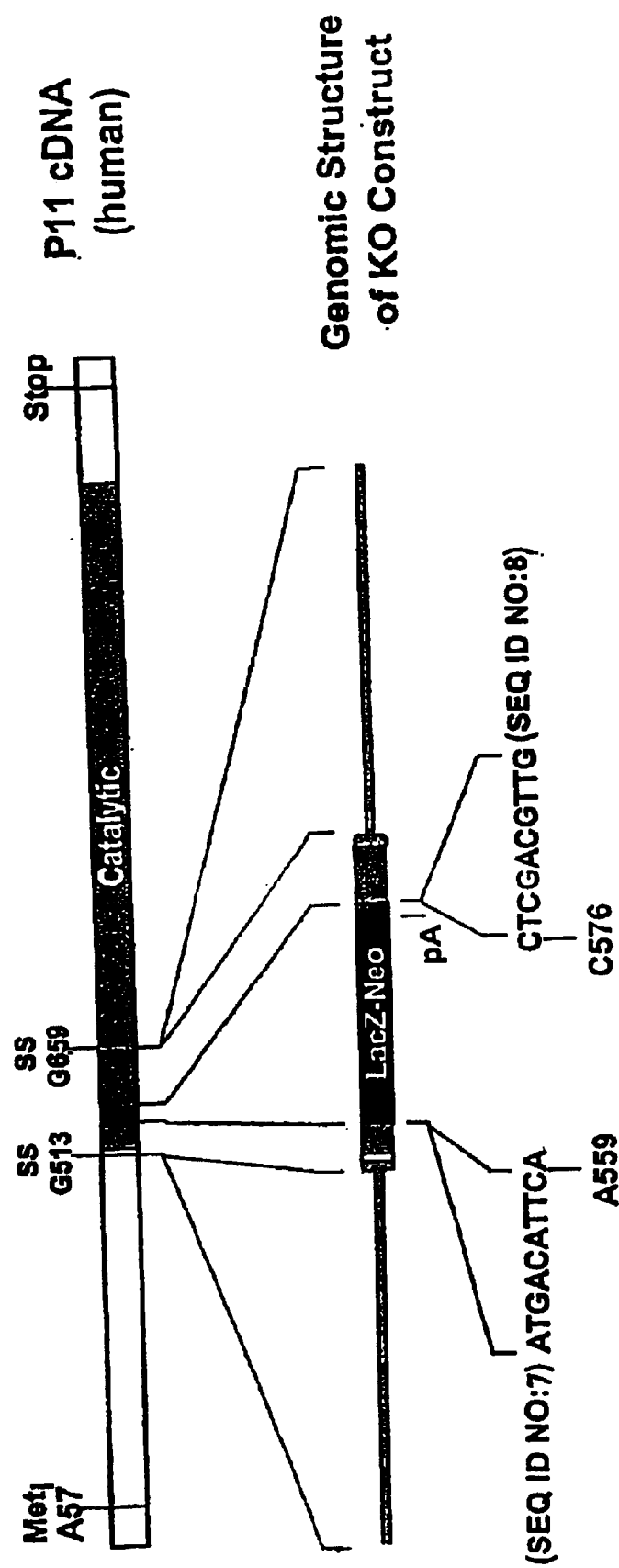
FIG. 1 shows a schematic depicting an exemplary PDE11A gene targeting or knockout (KO) construct which undergoes homologous recombination with a murine PDE11A sequence and deletes gene sequence corresponding to nucleotides 560–575 of the human cDNA sequence in which the ATG start site begins at position 57, replacing it with the LacZNeo sequence. The deleted portion of the gene comprises sequence encoding the catalytic domain of PDE11A. The sequences of the homology arms that flank the LacZ/Neo sequence are designated SEQ ID NO: 7 and SEQ ID NO: 8. SS refers to intron splice sites within the gene. pA refers to a polyadenylation signal.
Figure 3:
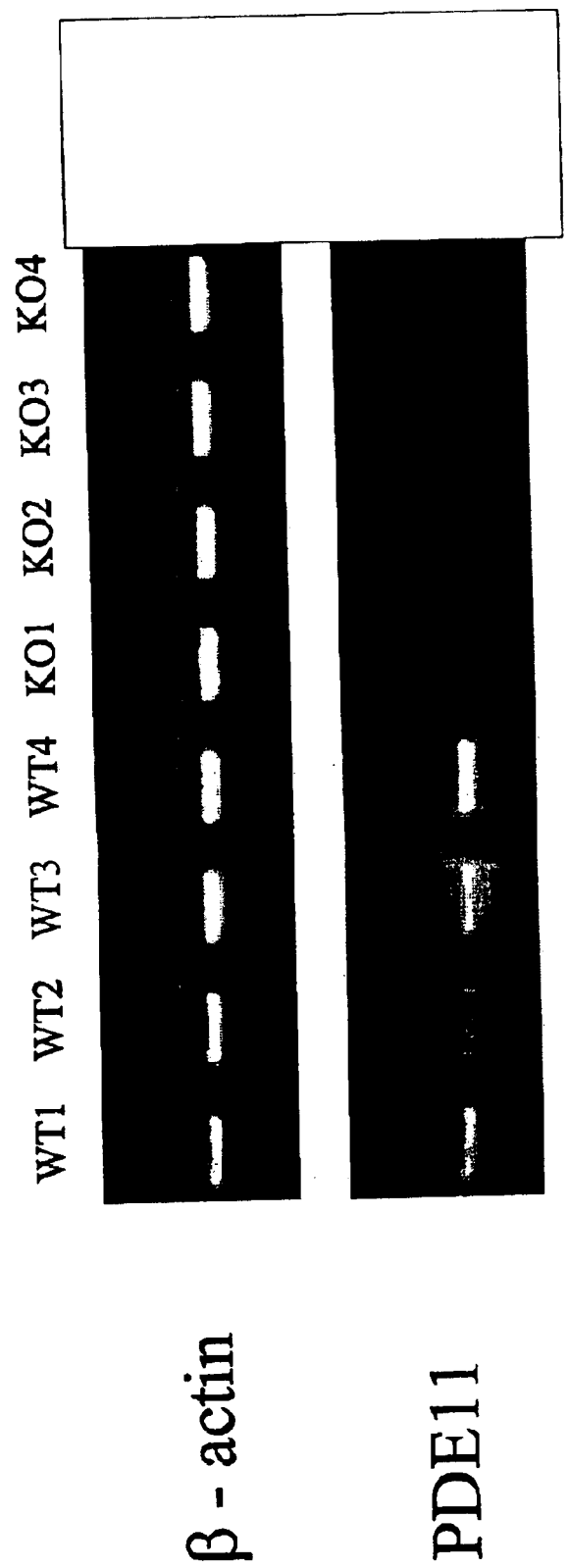
FIG. 3 shows an ethidium bromide-stained agarose gel illustrating the ablation of the PDE11 mRNA in the testis of PDE11 knockout (KO) mice. 5 μg of testis total RNA, extracted from 4 wild type (WT;=WT1, WT2, WT3 and WT4) and 4 PDE11 knockout mice (KO;=KO1, KO2, KO3 and KO4), was subjected to reverse transcription followed by PCR. Using PDE11-specific primers (designed across the site of insertion), the 4 wild type samples show the presence of the intact PDE11 transcript. This transcript is not detected in the PDE11 knockout samples. β-actin controls show equal loading of cDNA.

The present invention features genetically-modified animal cells and genetically-modified non-human mammals containing a disrupted PDE11A gene, as well as assays for identifying PDE11A function in the cells and tissues that normally express PDE11A.

Based upon studies of genetically-modified mice homozygous for a PDE11A disruption (PDE11A−/−), we have discovered that PDE11A plays a role in stimulating spermatogenesis. Accordingly, the present invention also provides methods for impacting or affecting, e.g., stimulating or inhibiting, spermatogenesis in a mammal by administering an agent that increases or decreases PDE11A activity, respectively.

1. Genetically-Modified Non-human Mammals and Animal Cells

The genetically-modified, non-human mammals and genetically-modified animal cells, including human cells, of the invention are heterozygous or homozygous for a modification that functionally disrupts the PDE11A gene. The animal cells may be derived by genetically engineering cells in culture, or, in the case of non-human mammalian cells, the cells may be isolated from genetically-modified, non-human mammals.

The PDE11A gene locus is functionally disrupted by one of the several techniques for genetic modification known in the art, including chemical mutagenesis (Rinchik, Trends in Genetics 7: 15–21, 1991, Russell, Environmental & Molecular Mutagenesis 23 (Suppl. 24) 23–29, 1994), irradiation (Russell, supra), transgenic expression of PDE11A gene antisense RNA, either alone or in combination with a catalytic RNA ribozyme sequence (Luyckx et al., Proc. Natl. Acad. Sci. 96: 12174–79, 1999; Sokol et al., Transgenic Research 5: 363–71, 1996; Efrat et al., Proc. Natl. Acad. Sci. USA 91: 2051–55, 1994; Larsson et al., Nucleic Acids Research 22: 2242–48, 1994) and, as further discussed below, the disruption of the PDE11A gene by the insertion of a foreign nucleic acid sequence into the PDE11A gene locus. Preferably, the foreign sequence is inserted by homologous recombination or by the insertion of a viral vector. Most preferably, the method of PDE11A gene disruption is homologous recombination and includes a deletion of a portion of the endogenous PDE11A gene sequence.

The integration of the foreign sequence functionally disrupts the PDE11A gene through one or more of the following mechanisms: by interfering with the PDE11A gene transcription or translation process (e.g., by interfering with promoter recognition, or by introducing a transcription termination site or a translational stop codon into the PDE11A gene); or by distorting the PDE11A gene coding sequence such that it no longer encodes a PDE11A polypeptide with normal function (e.g., by inserting a foreign coding sequence into the PDE11A gene coding sequence, by introducing a frameshift mutation or amino acid(s) substitution, or, in the case of a double crossover event, by deleting a portion of the PDE11A gene coding sequence that is required for expression of a functional PDE11A protein).

To insert a foreign sequence into a PDE11A gene locus in the genome of a cell, the foreign DNA sequence is introduced by any suitable method well known in the art such as electroporation, calcium-phosphate precipitation, retroviral infection, microinjection, biolistics, liposome transfection, DEAE-dextran transfection, or transferrinfection (see, e.g., Neumann et al., EMBO J. 1: 841–845, 1982; Potter et al., Proc. Natl. Acad. Sci USA 81: 7161–65, 1984; Chu et al., Nucleic Acids Res. 15: 1311–26, 1987; Thomas and Capecchi, Cell 51: 503–12, 1987; Baum et al., Biotechniques 17: 1058–62, 1994; Biewenga et al., J. Neuroscience Methods 71: 67–75, 1997; Zhang et al., Biotechniques 15: 868–72, 1993; Ray and Gage, Biotechniques 13: 598–603, 1992; Lo, Mol. Cell. Biol. 3: 1803–14, 1983; Nickoloff et al., Mol. Biotech. 10: 93–101, 1998; Linney et al., Dev. Biol. (Orlando) 213: 207–16, 1999; Zimmer and Gruss, Nature 338: 150–153, 1989; and Robertson et al., Nature 323: 445–48, 1986). The preferred method for introducing foreign DNA into a cell is electroporation.

A. Homologous Recombination

The method of homologous recombination targets the PDE11A gene for disruption by introducing a PDE11A gene targeting vector into a cell containing a PDE11A gene. The ability of the vector to target the PDE11A gene for disruption stems from using a nucleotide sequence in the vector that is homologous to the PDE11A gene. This homology region facilitates hybridization between the vector and the endogenous sequence of the PDE11A gene. Upon hybridization, the probability of a crossover event between the targeting vector and genomic sequences greatly increases. This crossover event results in the integration of the vector sequence into the PDE11A gene locus and the functional disruption of the PDE11A gene.

As those skilled in the art will appreciate, general principles regarding the construction of vectors used for targeting are reviewed in Bradley et al. (Biotechnol. 10: 534, 1992). Two different exemplary types of vector can be used to insert DNA by homologous recombination: an insertion vector or a replacement vector. An insertion vector is circular DNA that contains a region of PDE11A gene homology with a double stranded break. Following hybridization between the homology region and the endogenous PDE11A gene, a single crossover event at the double stranded break results in the insertion of the entire vector sequence into the endogenous gene at the site of crossover.

The more preferred vector to use for homologous recombination is a replacement vector, which is collinear rather than circular. Replacement vector integration into the PDE11A gene requires a double crossover event, i.e. crossing over at two sites of hybridization between the targeting vector and the PDE11A gene. This double crossover event results in the integration of vector sequence that is sandwiched between the two sites of crossover into the PDE11A gene and the deletion of the corresponding endogenous PDE11A gene sequence that originally spanned between the two sites of crossover (see, e.g., Thomas and Capecchi et al., Cell 51: 503–12, 1987; Mansour et al., Nature 336: 348–52, 1988; Mansour et al., Proc. Natl. Acad. Sci. USA 87: 7688–7692, 1990; and Mansour, GATA 7: 219–227, 1990).

A region of homology in a targeting vector is generally at least 100 nucleotides in length. Most preferably, the homology region is at least 1–5 kilobases (Kb) in length. There is no demonstrated minimum length or minimum degree of relatedness required for a homology region. However, one skilled in the art will recognize that targeting efficiency for homologous recombination will generally correspond with the length and the degree of relatedness between the targeting vector and the PDE11A gene locus. In the case where a replacement vector is used, and a portion of the endogenous PDE11A gene is deleted upon homologous recombination, an additional consideration is the size of the deleted portion of the endogenous PDE11A gene. If this portion of the endogenous PDE11A gene is greater than 1 Kb in length, then a targeting cassette with regions of homology that are longer than 1 Kb is recommended to enhance the efficiency of recombination. Further guidance regarding the selection and use of sequences effective for homologous recombination is described in the literature (see, e.g., Deng and Capecchi, Mol. Cell. Biol. 12: 3365–3371, 1992; Bollag et al., Annu. Rev. Genet. 23: 199–225, 1989; and Waldman and Liskay, Mol. Cell. Biol. 8: 5350–5357, 1988).

A wide variety of cloning vectors may be used as vector backbones in the construction of the PDE11A gene targeting vectors of the present invention, including pBluescript-related plasmids (e.g., Bluescript KS+11), pQE70, pQE60, pQE-9, pBS, pD10, phagescript, phiX174, pBK Phagemid, pNH8A, pNH16a, pNH18Z, pNH46A, ptrc99a, pKK223-3, pKK233-3, pDR540, and pRIT5 PWLNEO, pSV2CAT, pXT1, pSG (Stratagene), pSVK3, PBPV, PMSG, and pSVL, pBR322 and pBR322-based vectors, pBM9, pBR325, pKH47, pBR328, pHC79, phage Charon 28, pKB11, pKSV-10, pK19 related plasmids, pUC plasmids, and the pGEM series of plasmids. These vectors are available from a variety of commercial sources (e.g., Boehringer Mannheim Biochemicals, Indianapolis, Ind.; Qiagen, Valencia, Calif.; Stratagene, La Jolla, Calif.; Promega, Madison, Wis.; and New England Biolabs, Beverly, Mass.). However, any other vectors, e.g. plasmids, viruses, or parts thereof, may be used for propagation as long as they are replicable and viable in the desired host. The vector may also comprise sequences which enable it to replicate in the host whose genome is to be modified. The use of such a vector can expand the interaction period during which recombination can occur, increasing the efficiency of targeting (see Molecular Biology, ed. Ausubel et al, Unit 9.16, FIG. 9.16.1).

The specific host employed for propagating the targeting vectors of the present invention is not critical. Examples include *E coli* K12 RR1 (Bolivar et al., Gene 2: 95,1977), *E. coli* K12 HB101 (ATCC No. 33694), *E. coli* MM21 (ATCC No. 336780), *E. coli* DH1 (ATCC No. 33849), *E. coli* strain DH5α, and *E. coli* STBL2. Alternatively, hosts such as *C. cerevisiae* or *B. subtilis* can be used. The above-mentioned hosts are available commercially (e.g., Stratagene, La Jolla, Calif.; and Life Technologies, Rockville, Md.).

To create the targeting vector, a PDE11A gene targeting construct is added to an above-described vector backbone. The PDE11A gene targeting constructs of the invention have at least one PDE11A gene homology region. To make the PDE11A gene homology regions, a PDE11A gene-related sequence is used as a basis for producing polymerase chain reaction (PCR) primers. These primers are used to amplify the desired region of the PDE11A sequence by high fidelity PCR amplification (Mattila et al., Nucleic Acids Res. 19: 4967, 1991; Eckert and Kunkel 1: 17, 1991; and U.S. Pat. No. 4,683,202). The genomic sequence is obtained from a genomic clone library or from a preparation of genomic DNA, preferably from the animal species that is to be targeted for PDE11A gene disruption. PDE11A gene-related sequences have been reported in, e.g., Fawcett, 2000, (human PDE11A1, GenBank Accession No. AJ251509), WO 00/40733 (human PDE11A1 and PDE11A2), and Yuasa, 2000 (human PDE11A3 and PE11A4, GenBank Accession No. AB036704 and AB038041).

Preferably, the targeting constructs of the invention also include an exogenous nucleotide sequence encoding a positive marker protein. The stable expression of a positive marker after vector integration confers an identifiable characteristic on the cell without compromising cell viability. Therefore, in the case of a replacement vector, the marker gene is positioned between two flanking homology regions so that it integrates into the PDE11A gene following the double crossover event.

It is preferred that the positive marker protein is a selectable protein; the stable expression of such a protein in a cell confers a selectable phenotypic characteristic, i.e., the characteristic enhances the survival of the cell under otherwise lethal conditions. Thus, by imposing the selectable condition, one can isolate cells that stably express the positive selectable marker from other cells that have not successfully integrated the vector sequence on the basis of viability. Examples of positive selectable marker proteins (and their agents of selection) include Neo (G418 or kanamycin), Hyg (hygromycin), HisD (histidinol), Gpt (xanthine), Ble (bleomycin), and Hprt (hypoxanthine) (see, e.g., Capecchi and Thomas, U.S. Pat. No. 5,464,764, and Capecchi, Science 244: 1288–92, 1989). Other positive markers that may also be used as an alternative to a selectable marker include reporter proteins such as β-galactosidase, firefly luciferase, or green fluorescent protein (see, e.g., Current Protocols in Cytometry, Unit 9.5, and Current Protocols in Molecular Biology, Unit 9.6, John Wiley & Sons, New York, N.Y., 2000).

The above-described positive selection scheme does not distinguish between cells that have integrated the vector by targeted homologous recombination at the PDE11A gene locus versus random, non-homologous integration of vector sequence into any chromosomal position. Therefore, when using a replacement vector for homologous recombination, it is also preferred to include a nucleotide sequence encoding a negative selectable marker protein. Expression of a negative selectable marker causes a cell expressing the marker to lose viability when exposed to a certain agent (i.e., the marker protein becomes lethal to the cell under certain selectable conditions). Examples of negative selectable markers (and their agents of lethality) include herpes simplex virus thymidine kinase (gancyclovir or 1,2-deoxy-2-fluoro-α-d-arabinofuransyl-5-iodouracil), Hprt (6-thioguanine or 6-thioxanthine), and diphtheria toxin, ricin toxin, and cytosine deaminase (5-fluorocytosine).

The nucleotide sequence encoding the negative selectable marker is positioned outside of the two homology regions of the replacement vector. Given this positioning, cells will only integrate and stably express the negative selectable marker if integration occurs by random, non-homologous recombination; homologous recombination between the PDE11A gene and the two regions of homology in the targeting construct excludes the sequence encoding the negative selectable marker from integration. Thus, by imposing the negative condition, cells that have integrated the targeting vector by random, non-homologous recombination lose viability.

A combination of positive and negative selectable markers is a preferred selection scheme for making the genetically-modified non-human mammals and animal cells of the invention because a series of positive and negative selection steps can be designed to more efficiently select only those cells that have undergone vector integration by homologous recombination, and, therefore, have a potentially disrupted PDE11A gene. Further examples of positive-negative selection schemes, selectable markers, and targeting constructs are described, for example, in U.S. Pat. No. 5,464,764, WO 94/06908, and Valancius and Smithies, Mol. Cell. Biol. 11:1402, 1991.

In order for a marker protein to be stably expressed upon vector integration, the targeting vector may be designed so that the marker coding sequence is operably linked to the endogenous PDE11A gene promoter upon vector integration. Expression of the marker is then driven by the PDE11A gene promoter in cells that normally express PDE11A gene. Alternatively, each marker in the targeting construct of the vector may contain its own promoter that drives expression independent of the PDE11A gene promoter. This latter scheme has the advantage of allowing for expression of markers in cells that do not typically express the PDE11A gene (Smith and Berg, Cold Spring Harbor Symp. Quant. Biol. 49: 171, 1984; Sedivy and Sharp, Proc. Natl. Acad. Sci. (USA) 86: 227: 1989; Thomas and Capecchi, Cell 51: 503, 1987).

Exogenous promoters that can be used to drive marker gene expression include cell-specific or stage-specific promoters, constitutive promoters, and inducible or regulatable promoters. Non-limiting examples of these promoters include the herpes simplex thymidine kinase promoter, cytomegalovirus (CMV) promoter/enhancer, SV40 promoters, PGK promoter, PMC1-neo, metallothionein promoter, adenovirus late promoter, vaccinia virus 7.5K promoter, avian beta globin promoter, histone promoters (e.g., mouse histone H3-614), beta actin promoter, neuron-specific enolase, muscle actin promoter, and the cauliflower mosaic virus 35S promoter (see, generally, Sambrook et al., *Molecular Cloning*, Vols. I–III, Cold Spring Harbor Laboratory Press, Cold Spring Harbor, N.Y., 1989, and *Current Protocols in Molecular Biology*, John Wiley & Sons, New York, N.Y., 2000; Stratagene, La Jolla, Calif.).

To confirm whether cells have integrated the vector sequence into the targeted PDE11A gene locus, primers or genomic probes that are specific for the desired vector integration event can be used in combination with PCR or Southern blot analysis to identify the presence of the desired vector integration into the PDE11A gene locus (Erlich et al., Science 252: 1643–51, 1991; Zimmer and Gruss, Nature 338: 150, 1989; Mouellic et al., Proc. Natl. Acad. Sci. (USA) 87: 4712, 1990; and Shesely et al., Proc. Natl. Acad. Sci. (USA) 88: 4294, 1991).

B. Gene Trapping

Another method available for inserting a foreign nucleic acid sequence into the PDE11A gene locus to functionally disrupt the PDE11A gene is gene trapping. This method takes advantage of the cellular machinery present in all mammalian cells that splices exons into mRNA to insert a gene trap vector coding sequence into a gene in a random fashion. Once inserted, the gene trap vector creates a mutation that may functionally disrupt the trapped PDE11A gene. In contrast to homologous recombination, this system for mutagenesis creates largely random mutations. Thus, to obtain a genetically-modified cell that contains a functionally disrupted PDE11A gene, cells containing this particular mutation must be identified and selected from a pool of cells that contain random mutations in a variety of genes.

Gene trapping systems and vectors have been described for use in genetically modifying murine cells and other cell types (see, e.g., Allen et al., Nature 333: 852–55, 1988; Bellen et al., Genes Dev. 3: 1288–1300, 1989; Bier et al., Genes Dev. 3: 1273–1287, 1989; Bonnerot et al., J. Virol. 66: 4982–91, 1992; Brenner et al., Proc. Nat. Acad. Sci. USA 86: 5517–21, 1989; Chang et al., Virology 193: 737–47, 1993; Friedrich and Soriano, Methods Enzymol. 225: 681–701, 1993; Friedrich and Soriano, Genes Dev. 5: 1513–23, 1991; Goff, Methods Enzymol. 152: 469–81, 1987; Gossler et al., Science 244: 463–65, 1989; Hope, Develop. 113: 399–408, 1991; Kerr et al., Cold Spring Harb. Symp. Quant. Biol. 2: 767–776, 1989; Reddy et al., J. Virol. 65: 1507–1515, 1991; Reddy et al., Proc. Natl. Acad. Sci.

U.S.A. 89: 6721–25, 1992; Skarnes et al., Genes Dev. 6: 903–918, 1992; von Melchner and Ruley, J. Virol. 63: 3227–3233, 1989; and Yoshida et al., Transgen. Res. 4: 277–87, 1995).

Promoter trap (5' trap) vectors contain, in 5' to 3' order, a splice acceptor sequence followed by an exon, which is typically characterized by a translation initiation codon and open reading frame and/or an internal ribosome entry site. In general, these promoter trap vectors do not contain promoters or operably linked splice donor sequences. Consequently, after integration into the cellular genome of the host cell, the promoter trap vector sequence intercepts the normal splicing of the upstream gene and acts as a terminal exon. Expression of the vector coding sequence is dependent upon the vector integrating into an intron of the disrupted gene in the proper reading frame. In such a case, the cellular splicing machinery splices exons from the trapped gene upstream of the vector coding sequence (Zambrowicz et al., WO 99/50426).

An alternative method for producing an effect similar to the above-described promoter trap vector is a vector that incorporates a nested set of stop codons present in, or otherwise engineered into, the region between the splice acceptor of the promoter trap vector and the translation initiation codon or polyadenylation sequence. The coding sequence can also be engineered to contain an independent ribosome entry site (IRES) so that the coding sequence will be expressed in a manner largely independent of the site of integration within the host cell genome. Typically, but not necessarily, an IRES is used in conjunction with a nested set of stop codons.

Another type of gene trapping scheme uses a 3' gene trap vector. This type of vector contains, in operative combination, a promoter region, which mediates expression of an adjoining coding sequence, the coding sequence, and a splice donor sequence that defines the 3' end of the coding sequence exon. After integration into a host cell genome, the transcript expressed by the vector promoter is spliced to a splice acceptor sequence from the trapped gene that is located downstream of the integrated gene trap vector sequence. Thus, the integration of the vector results in the expression of a fusion transcript comprising the coding sequence of the 3' gene trap cassette and any downstream cellular exons, including the terminal exon and its polyadenylation signal. When such vectors integrate into a gene, the cellular splicing machinery splices the vector coding sequence upstream of the 3' exons of the trapped gene. One advantage of such vectors is that the expression of the 3' gene trap vectors is driven by a promoter within the gene trap cassette and does not require integration into a gene that is normally expressed in the host cell (Zambrowicz et al., WO 99/50426). Examples of transcriptional promoters and enhancers that may be incorporated into the 3' gene trap vector include those discussed above with respect to targeting vectors.

The viral vector backbone used as the structural component for the promoter or 3' gene trap vector may be selected from a wide range of vectors that can be inserted into the genome of a target cell. Suitable backbone vectors include, but are not limited to, herpes simplex virus vectors, adenovirus vectors, adeno-associated virus vectors, retroviral vectors, lentiviral vectors, pseudorabies virus, alpha-herpes virus vectors, and the like. A thorough review of viral vectors, in particular, viral vectors suitable for modifying nonreplicating cells and how to use such vectors in conjunction with the expression of an exogenous polynucleotide sequence, can be found in *Viral Vectors: Gene Therapy and Neuroscience Applications*, Eds. Caplitt and Loewy, Academic Press, San Diego, 1995.

Preferably, retroviral vectors are used for gene trapping. These vectors can be used in conjunction with retroviral packaging cell lines such as those described in U.S. Pat. No. 5,449,614. Where non-murine mammalian cells are used as target cells for genetic modification, amphotropic or pantropic packaging cell lines can be used to package suitable vectors (Ory et al., Proc. Natl. Acad. Sci., USA 93: 11400–11406, 1996). Representative retroviral vectors that can be adapted to create the presently described 3' gene trap vectors are described, for example, in U.S. Pat. No. 5,521, 076.

The gene trapping vectors may contain one or more of the positive marker genes discussed above with respect to targeting vectors used for homologous recombination. Similar to their use in targeting vectors, these positive markers are used in gene trapping vectors to identify and select cells that have integrated the vector into the cell genome. The marker gene may be engineered to contain an IRES so that the marker will be expressed in a manner largely independent of the location in which the vector has integrated into the target cell genome.

Given that gene trap vectors will integrate into the genome of infected host cells in a fairly random manner, a genetically-modified cell having a disrupted PDE11A gene must be identified from a population of cells that have undergone random vector integration. Preferably, the genetic modifications in the population of cells are of sufficient randomness and frequency such that the population represents mutations in essentially every gene found in the cell's genome, making it likely that a cell with a disrupted PDE11A gene will be identified from the population (see Zambrowicz et al., WO 99/50426; Sands et al., WO 98/14614).

Individual mutant cell lines containing a disrupted PDE11A gene are identified in a population of mutated cells using, for example, reverse transcription and PCR to identify a mutation in a PDE11A gene sequence. This process can be streamlined by pooling clones. For example, to find an individual clone containing a disrupted PDE11A gene, RT-PCR is performed using one primer anchored in the gene trap vector and the other primer located in the PDE11A gene sequence. A positive RT-PCR result indicates that the vector sequence is encoded in the PDE11A gene transcript, indicating that PDE11A gene has been disrupted by a gene trap integration event (see, e.g., Sands et al., WO 98/14614).

C. Temporal, Spatial, and Inducible PDE11A Gene Disruptions

In certain embodiments of the present invention, a functional disruption of the endogenous PDE11A gene occurs at specific developmental or cell cycle stages (temporal disruption) or in specific cell types (spatial disruption). In other embodiments, the PDE11A gene disruption is inducible when certain conditions are present. A recombinase excision system, such as a Cre-Lox system, may be used to activate or inactivate the PDE11A gene at a specific developmental stage, in a particular tissue or cell type, or under particular environmental conditions. Generally, methods utilizing Cre-Lox technology are carried out as described by Torres and Kuhn, *Laboratory Protocols for Conditional Gene Targeting*, Oxford University Press, 1997. Methodology similar to that described for the Cre-Lox system can also be employed utilizing the FLP-FRT system. The FLP-FRT system and further guidance regarding the use of recombinase excision systems for conditionally disrupting genes by homologous recombination or viral insertion are provided, for example, in U.S. Pat. Nos. 5,626,159, 5,527,695, and 5,434,066, WO 98/29533, Orban et al., Proc. Nat. Acad. Sci. USA 89: 6861–65, 1992; O'Gorman et al., Science 251: 1351–55, 1991; Sauer et al., Nucleic Acids Research 17: 147–61, 1989; Barinaga, Science 265: 26–28, 1994; and Akagi et al., Nucleic Acids Res. 25: 1766–73, 1997. More than one recombinase system can be used to genetically modify a non-human mammal or animal cell.

When using homologous recombination to disrupt the PDE11A gene in a temporal, spatial, or inducible fashion, using a recombinase system such as the Cre-Lox system, a portion of the PDE11A gene coding region is replaced by a targeting construct comprising the PDE11A gene coding region flanked by loxP sites. Non-human mammals and animal cells carrying this genetic modification contain a functional, loxP-flanked PDE11A gene. The temporal, spatial, or inducible aspect of the PDE11A gene disruption is caused by the expression pattern of an additional transgene, a Cre recombinase transgene, that is expressed in the non-human mammal or animal cell under the control of the desired spatially-regulated, temporally-regulated, or inducible promoter, respectively. A Cre recombinase targets the loxP sites for recombination. Therefore, when Cre expression is activated, the LoxP sites undergo recombination to excise the sandwiched PDE11A gene coding sequence, resulting in a functional disruption of the PDE11A gene (Rajewski et al., J. Clin. Invest. 98: 600–03, 1996; St.-Onge et al., Nucleic Acids Res. 24: 3875–77, 1996; Agah et al., J. Clin. Invest. 100: 169–79, 1997; Brocard et al., Proc. Natl. Acad. Sci. USA 94: 14559–63, 1997; Feil et al., Proc. Natl. Acad. Sci. USA 93: 10887–90, 1996; and Kühn et al., Science 269: 1427–29, 1995).

A cell containing both a Cre recombinase transgene and loxP-flanked PDE11A gene can be generated through standard transgenic techniques or, in the case of genetically-modified, non-human mammals, by crossing genetically-modified, non-human mammals wherein one parent contains a loxP flanked PDE11A gene and the other contains a Cre recombinase transgene under the control of the desired promoter. Further guidance regarding recombinase systems and specific promoters useful to temporally, spatially, or conditionally disrupt the PDE11A gene is found, for example, in Sauer, Meth. Enz. 225: 890–900, 1993, Gu et al., Science 265: 103–06, 1994, Araki et al., J. Biochem. 122: 977–82, 1997, Dymecki, Proc. Natl. Acad. Sci. 93: 6191–96, 1996, and Meyers et al., Nature Genetics 18: 136–41, 1998.

An inducible disruption of the PDE11A gene can also be achieved by using a tetracycline responsive binary system (Gossen and Bujard, Proc. Natl. Acad. Sci. USA 89: 5547–51, 1992). This system involves genetically modifying a cell to introduce a Tet promoter into the endogenous PDE11A gene regulatory element and a transgene expressing a tetracycline-controllable repressor (TetR). In such a cell, the administration of tetracycline activates the TetR which, in turn, inhibits PDE11A gene expression and, therefore, functionally disrupts the PDE11A gene (St.-Onge et al., Nucleic Acids Res. 24: 3875–77, 1996, U.S. Pat. No. 5,922,927).

The above-described systems for temporal, spatial, and inducible disruptions of the PDE11A gene can also be adopted when using gene trapping as the method of genetic modification, for example, as described, for example, in WO 98/29533.

D. Creating Genetically-Modified, Non-human Mammals and Animal Cells

The above-described methods for genetic modification can be used to functionally disrupt a PDE11A gene in virtually any type of somatic or stem cell derived from an animal. Genetically-modified animal cells of the invention include, but are not limited to, mammalian cells, including human cells, and avian cells. These cells may be derived from genetically engineering any animal cell line, such as culture-adapted, tumorigenic, or transformed cell lines, or they may be isolated from a genetically-modified, non-human mammal carrying the desired PDE11A genetic modification.

The cells may be heterozygous or homozygous for the disrupted PDE11A gene. To obtain cells that are homozygous for the PDE11A gene disruption (PDE11A−/−), direct, sequential targeting of both alleles can be performed. This process can be facilitated by recycling a positive selectable marker. According to this scheme the nucleotide sequence encoding the positive selectable marker is removed following the disruption of one allele using the Cre-Lox P system. Thus, the same vector can be used in a subsequent round of targeting to disrupt the second PDE11A gene allele (Abuin and Bradley, Mol. Cell. Biol. 16: 1851–56, 1996; Sedivy et al., T.I.G. 15: 88–90, 1999; Cruz et al., Proc. Natl. Acad. Sci. (USA) 88: 7170–74, 1991; Mortensen et al., Proc. Natl. Acad. Sci. (USA) 88: 7036–40, 1991; te Riele et al., Nature (London) 348: 649–651, 1990).

An alternative strategy for obtaining ES cells that are PDE−/− is the homogenotization of cells from a population of cells that is heterozygous for the PDE11A gene disruption (PDE11A+/−). The method uses a scheme in which PDE11A+/− targeted clones that express a selectable drug resistance marker are selected against a very high drug concentration; this selection favors cells that express two copies of the sequence encoding the drug resistance marker and are, therefore, homozygous for the PDE11A gene disruption (Mortensen et al., Mol. Cell. Biol. 12: 2391–95, 1992). In addition, genetically-modified animal cells can be obtained from genetically-modified PDE11A−/− non-human mammals that are created by mating non-human mammals that are PDE11A+/− in germline cells, as further discussed below.

Following the genetic modification of the desired cell or cell line, the PDE11A gene locus can be confirmed as the site of modification by PCR analysis according to standard PCR or Southern blotting methods known in the art (see, e.g., U.S. Pat. No. 4,683,202; and Erlich et al., Science 252: 1643, 1991). Further verification of the functional disruption of the PDE11A gene may also be made if PDE11A gene messenger RNA (mRNA) levels and/or PDE11A polypeptide levels are reduced in cells that normally express the PDE11A gene. Measures of PDE11A gene mRNA levels may be obtained by using reverse transcriptase mediated polymerase chain reaction (RT-PCR), Northern blot analysis, or in situ hybridization. The quantification of PDE11A polypeptide levels produced by the cells can be made, for example, by standard immunoassay methods known in the art. Such immunoassays include, but are not limited to, competitive and non-competitive assay systems using techniques such as radioimmunoassays, ELISA (enzyme-linked immunosorbent assay), "sandwich" immunoassays, immunoradiometric assays, gel diffusion precipitin reactions, immunodiffusion assays, in situ immunoassays (using colloidal gold, enzymatic, or radioisotope labels, for example), Western blots, 2-dimensional gel analysis, precipitation reactions, immunofluorescence assays, protein A assays, and immunoelectrophoresis assays.

Preferred genetically-modified animal cells are ES cells and ES-like cells. These cells are derived from the preimplantation embryos and blastocysts of various species, such as mice (Evans et al., Nature 129:154–156, 1981; Martin, Proc. Natl. Acad. Sci., USA, 78: 7634–7638, 1981), pigs and sheep (Notanianni et al., J. Reprod. Fert. Suppl., 43: 255–260, 1991; Campbell et al., Nature 380: 64–68,1996) and primates, including humans (Thomson et al., U.S. Pat. No. 5,843,780, Thomson et al., Science 282: 1145–1147, 1995; and Thomson et al., Proc. Natl. Acad. Sci. USA 92: 7844–7848, 1995).

These types of cells are pluripotent. That is, under proper conditions, they differentiate into a wide variety of cell types derived from all three embryonic germ layers: ectoderm, mesoderm and endoderm. Depending upon the culture conditions, a sample of ES cells can be cultured indefinitely as stem cells, allowed to differentiate into a wide variety of different cell types within a single sample, or directed to differentiate into a specific cell type, such as macrophage-like cells, neuronal cells, cardiomyocytes, adipocytes, smooth muscle cells, endothelial cells, skeletal muscle cells, keratinocytes, and hematopoietic cells, such as eosinophils, mast cells, erythroid progenitor cells, or megakaryocytes. Directed differentiation is accomplished by including specific growth factors or matrix components in the culture conditions, as further described, for example, in Keller et al., Curr. Opin. Cell Biol. 7: 862–69, 1995, Li et al., Curr. Biol. 8: 971, 1998, Klug et al., J. Clin. Invest. 98: 216–24, 1996, Lieschke et al., Exp. Hematol. 23: 328–34, 1995, Yamane et al., Blood 90: 3516–23, 1997, and Hirashima et al., Blood 93: 1253–63, 1999.

The particular embryonic stem cell line that is used for genetic modification is not critical; exemplary murine ES cell lines include AB-1 (McMahon and Bradley, Cell 62:1073–85, 1990), E14 (Hooper et al., Nature 326: 292–95, 1987), D3 (Doetschman et al., J. Embryol. Exp. Morph. 87: 27–45, 1985), CCE (Robertson et al, Nature 323: 445–48, 1986), RW4 (Genome Systems, St. Louis, Mo.), and DBA/1lacJ (Roach et al., Exp. Cell Res. 221: 520–25, 1995). Genetically-modified murine ES cells may be used to generate genetically-modified mice, according to published procedures (Robertson, 1987, *Teratocarcinomas and Embryonic Stem Cells: A Practical Approach*, Ed. E. J. Robertson, Oxford: IRL Press, pp. 71–112, 1987; Zjilstra et al., Nature 342: 435–438, 1989; and Schwartzberg et al., Science 246: 799–803, 1989).

Following confirmation that the ES cells contain the desired functional disruption of the PDE11A gene, these ES cells are then injected into suitable blastocyst hosts for generation of chimeric mice according to methods known in the art (Capecchi, Trends Genet. 5: 70, 1989). The particular mouse blastocysts employed in the present invention are not critical. Examples of such blastocysts include those derived from C57BL/6 mice, C57BL/6 Albino mice, Swiss outbred mice, CFLP mice, and MFI mice. Alternatively, ES cells may be sandwiched between tetraploid embryos in aggregation wells (Nagy et al., Proc. Natl. Acad. Sci. USA 90: 8424–8428, 1993).

The blastocysts or embryos containing the genetically-modified ES cells are then implanted in pseudopregnant female mice and allowed to develop in utero (Hogan et al., *Manipulating the Mouse Embryo: A Laboratory Manual*, Cold Spring Harbor Laboratory, 1988; and *Teratocarcinomas and Embryonic Stem Cells: A Practical Approach*, E. J. Robertson, ed., IRL Press, Washington, D.C., 1987). The offspring born to the foster mothers may be screened to identify those that are chimeric for the PDE11A gene disruption. Generally, such offspring contain some cells that are derived from the genetically-modified donor ES cell as well as other cells from the original blastocyst. In such circumstances, offspring may be screened initially for mosaic coat color, where a coat color selection strategy has been employed, to distinguish cells derived from the donor ES cell from the other cells of the blastocyst. Alternatively, DNA from tail tissue of the offspring can be used to identify mice containing the genetically-modified cells.

The mating of chimeric mice that contain the PDE11A gene disruption in germ line cells produces progeny that possess the PDE11A gene disruption in all germ line cells and somatic cells. Mice that are heterozygous for the PDE11A gene disruption can then be crossed to produce homozygotes (see, e.g., U.S. Pat. Nos. 5,557,032, and 5,532, 158).

An alternative to the above-described ES cell technology for transferring a genetic modification from a cell to a whole animal is to use nuclear transfer. This method can be employed to make other genetically-modified, non-human mammals besides mice, for example, sheep (McCreath et al., Nature 29: 1066–69, 2000; Campbell et al., Nature 389: 64–66, 1996; and Schnieke et al., Science 278: 2130–33, 1997) and calves (Cibelli et al., Science 280: 1256–58, 1998). Briefly, somatic cells (e.g., fibroblasts) or pluripotent stem cells (e.g., ES-like cells) are selected as nuclear donors and are genetically-modified to contain a functional disruption of the PDE11A gene. When inserting a DNA vector into a somatic cell to mutate the PDE11A gene, it is preferred that a promoterless marker be used in the vector such that vector integration into the PDE11A gene results in expression of the marker under the control of the PDE11A gene promoter (Sedivy and Dutriaux, T.I.G. 15: 88–90, 1999; McCreath et al., Nature 29: 1066–69, 2000). Nuclei from donor cells which have the appropriate PDE11A gene disruption are then transferred to fertilized or parthenogenetic oocytes that are enucleated (Campbell et al., Nature 380: 64, 1996; Wilmut et al., Nature 385: 810, 1997). Embryos are reconstructed, cultured to develop into the morula/blastocyst stage, and transferred into foster mothers for full term in utero development.

The present invention also encompasses the progeny of the genetically-modified, non-human mammals and genetically-modified animal cells. While the progeny are heterozygous or homozygous for the genetic modification that functionally disrupts the PDE11A gene, they may not be genetically identical to the parent non-human mammals and animal cells due to mutations or environmental influences that may occur in succeeding generations at other loci in addition to the genetic modification presently described.

E. "Humanized" Non-human Mammals and Animal Cells

The genetically-modified non-human mammals and non-human animal cells of the invention containing a disrupted endogenous PDE11A gene can be further modified to express the human PDE11A sequence (referred to herein as "humanized"). The human PDE11A sequence is disclosed, for example, in Fawcett, 2000, Phillips et al., WO 00/40733, and GenBank Accession No. AJ251509.

A preferred method for humanizing cells involves substituting the human PDE11A sequence for the endogenous PDE11A by homologous recombination. The targeting vectors are similar to those traditionally used as knock out vectors with respect to the 5' and 3' homology arms and positive/negative selection schemes. However, the vectors also include sequences that, upon recombination, insert the human PDE11A coding sequence in exchange for the endogenous sequence, or affect base pair changes, codon substitutions, or exon substitutions, that modify the endogenous sequence such that the sequence encodes the human PDE11A instead of the endogenous wild type sequence.

Once homologous recombinants have been identified, it is possible to excise any inserted selection-based sequences (e.g., neo) by using Cre or Flp-mediated site directed recombination (Dymecki, Proc. Natl. Acad. Sci. 93: 6191–96, 1996).

It is preferred that the human PDE sequence be positioned directly downstream of the endogenous translation start site. This positioning preserves the endogenous temporal and spatial expression patterns of the PDE11A gene. The human sequence can comprise the whole genomic PDE11A sequence, or the full length human cDNA sequence with a polyA tail attached at the 3' end for proper processing (Shiao et al., Transgenic Res. 8: 295–302, 1999). Further guidance regarding these methods of genetically modifying cells and non-human mammals to replace expression of an endogenous gene with its human counterpart is found, for example, in Sullivan et al., J. Biol. Chem. 272: 17972–80, 1997, Reaume et al., J. Biol. Chem. 271: 23380–88, 1996, and Scott et al., U.S. Pat. No. 5,777,194.

Another method for creating such "humanized" organisms is a multi-step process involving, first, the creation of PDE11A−/− embryos, and, second, the introduction of a transgene encoding the human sequence into the PDE11A−/− embryos.

EXAMPLE
Generation of PDE11A+/− and PDE11A−/− Mice.

Genetically-modified mouse ES cells (PDE11A+/−) were generated using the scheme shown in FIG. 1(DeltaGen, Menlo Park, Calif.). A partial cDNA sequence of the human PDE11A gene (FIG. 2A; SEQ ID NOS: 1 and 2) was used to design oligonucleotide strands 7744 and 7745 as shown below.

```
Oligonucleotide 7744-
5' TTTCTGTACCATCCCCAGCTCCATG 3'     (SEQ ID NO:3)

Oligonucleotide 7745-
5' AAGGCAGCCAACATCCCTCTGGTGT 3'     (SEQ ID NO:4)
```

PCR based amplification of mouse genomic DNA using the above primers generated the product representing the mouse PDE11A sequence shown in FIG. 2B (SEQ ID NOS: 5 and 6). Based upon this genomic sequence, a targeting construct was created which contained two homology arms (each of 10 nucleotides in length) of SEQ ID NOS: 7 and 8, and a LacZ-Neo sequence inserted between the arms, as shown in FIG. 1. DNA containing the targeting construct was inserted into the ES cells by electroporation. Integration of this construct into the murine PDE11A gene in ES R1 cells (Deng et al., Dev. Biol. 185: 42–54, 1997; Udy et al., Exp. Cell Res. 231: 296–301, 1997) resulted in the replacement of the nucleotides 27–42 of SEQ ID NOS: 5 and 6 with the LacZ-Neo gene. ES cells that were neomycin resistant were analyzed by Southern blot to confirm disruption of a PDE11A gene. These targeted ES cells were then used for generation of chimeric mice by injecting the cells into blastocysts and implanting the blastocysts into pseudopregnant female mice (Capecchi et al., Trends Genet. 5: 70, 1989, Hogan et al., *Manipulating the Mouse Embryo: A Laboratory Manual*, Cold Spring Harbor Laboratory, 1988; and *Teratocarcinomas and Embryonic Stem Cells: A Practical Approach*, E. J. Robertson, ed., IRL Press, Washington, D.C., 1987). Chimeric mice were then bred with C57BL/6 (Jackson Laboratories, Bar Harbor, Me.) mice to create F1 PDE+/− heterozygotes, which were in turn bred to produce F2 PDE−/− homozygotic mice. The functional disruption of the PDE11A gene in the heterozygotes and homozygotes was confirmed by PCR and Southern blot analysis.

2. Characterization of PDE11A Function and Therapeutic Relevance

Perturbations that modulate PDE11A activity or expression can be induced in cells, tissues, or mammals to determine whether PDE11A modulation produces a physiologically relevant effect or phenotype. One means of inducing such a perturbation is genetically modifying a non-human mammal or animal cell to disrupt the PDE11A gene. Alternatively, an agent that modulates PDE11A activity or expression can be administered to determine its effect on a cell or tissue preparation, or on a mammal.

A. Tissue Expression

Guidance for determining which cells, tissues, or phenotypes to study with respect to PDE11A function is found in the PDE11A expression pattern in species such as mice and humans. In addition to what has previously been described for human PDE11A expression in Fawcett, 2000, (i.e., testis, skeletal muscle, kidney, liver, various glandular tissue (e.g., pituitary, salivary, adrenal, mammary, and thyroid), pancreas, spinal cord, and trachea), we hereby disclose additional tissues that express PDE11A, and further characterize expression in the previously disclosed tissues.

PDE11A expression patterns were determined in formalin-fixed, paraffin-embedded normal human tissues sectioned at a width of 5 $\mu$m (Peterborough Hospital Cellular Pathology Services, Peterborough, UK), and paraformaldehyde-fixed, paraffin-embedded normal mouse testis samples sectioned at 7 $\mu$M (Cat. No. 69584-3, Novagen, Madison, Wis.). The immobilized sections were dewaxed by washing in xylene (5 min.), absolute alcohol (5 min.), and then industrial methylated spirits (5 min.) Afterwards the slides were washed for 5 min. in running water, then treated for antigen retrieval according to one of the following methods: 1) treated with trypsin for 15 min. at 37° C. (Cat. No. T7168, Sigma Chemicals, St. Louis, Mo., 1 tablet/ml water), followed by another wash in running water; or 2) treated with target retrieval solution (Cat. No. S1700, DAKO Corp., Carpinteria, Calif.) using the steamer method as per manufacturer's instructions, followed by several washes in tris-buffered saline (TBS) (Cat. No. T6664, Sigma Chemicals, St. Louis, Mo., 1 sachet/L water). Samples were soaked in fresh TBS and treated with the components of one of two alternative immunohistochemical kits, as indicated below.

Samples were incubated with a primary rabbit anti-PDE11A antibody (1:500 or 1:000 dilution, in TBS/5% nonfat milk for 60 min.) The primary antibody was raised against the human PDE11A (GenBank Accession No. AJ251509) catalytic domain peptide sequence of SAIFDRNRKDELPRL (SEQ ID NO: 9) (Cambridge Research Biochemicals, Cleveland, UK). The antibody detection system included either: 1) an anti-rabbit secondary antibody conjugate to horseradish peroxidase (HRP) and a 3,3'-diaminobenzidine (DAB) chromogen solution (Cat. No. K4010, DAKO EnVision™+System, DAKO Corp.); or 2) an anti-rabbit secondary antibody conjugated to alkaline phosphatase (AP) (Cat. No.-AK5001, ABC-AP kit, Vector Laboratories, Burlingame, Calif.) and an AP substrate kit (Cat. No. SK-5100, Vector® Red, Vector Laboratories). The immunohistochemical procedures were conducted according to manufacturers' recommendations. Following incubation with the chromogen, tissues were counterstained with hemotoxylin (Cat. No. H3401, Vector Laboratories). The samples were then rinsed in water and dipped 10 times (10×) in acid rinse (2% v/v glacial acetic acid), followed by 10× in water, 20× in Scott's tap water (Cat. No. 6769002, Shandon Scientific, Runcorn, UK), rinsed 3 min. in water, dehydrated, mounted in DPX (Cat. No. 360294H, BDH Laboratory Supplies, Poole, UK), and sealed with a coverslip.

Strong PDE11A antibody staining was demonstrated in the following cell types and structures: cardiac myocytes in all chambers of the heart; endothelial cells lining the endocardium; medial smooth muscle cells of the cardiac (epicardial and intromyocardial) and systemic vasculature in venules, veins, arterioles, and arteries (particularly in vessels of smaller diameter), vascular endothelial cells; Schwann cells and perineural cells (nerve and vascular staining often correlated in particular tissues, e.g., bladder, testis, and heart); in the testis, in nuclei of spermatogonia, as well as spermocytes and spermatids, interstitial Leydig cells and cells underlying the basement membrane of the seminiferous tubules (fibroblasts), and in the vascular smooth muscle; amine precursor uptake and decarboxylation (APUD) enteroendocrine cells in the colon and rectal glands; neurons throughout the brain (moderate to strong staining), such as in the substantia nigra, amygdyla, nucleus basalis, the area postrema, and in acidophiles (somatotrophs and lactotrophs) of the anterior pituitary (especially in the periphery of the lateral zones); alveolar macrophages in the lung; islet cells in the pancreas; rare cells in the red pulp of the spleen; in numerous adipocytes; in lymphoid tissue; and in samples from cancerous prostate, hyperplastic prostate, and skin with malignant melanoma.

Additional cell types and tissues that showed moderate to weak staining for PDE11A included the following: the bladder urothelium, especially the basal to transitional epithelial layers (in the cytoplasm and, especially, in the nuclei of cells); cells in the exocrine parenchyma; keratinocytes in the basal and prickle layers of the epidermis; the cortex, outer root sheath, and collagenous root sheath of the hair follicle; eccrine glands; occasional Purkinje cells in the cerebellum; ependymal cells, cells in the basal ganglia and striatum; ganglion cells in Auerbach's plexus and Meissner's plexus; synovial cells; hepatocytes; smooth muscle; pleural mesothelium; squamous cells in the vaginal mucosa; lobular and ductal epithelial cells in the breast; vascular and sinusoidal lining cells in the splenic red pulp; sebaceous glands; convoluted tubules and collecting ducts in the kidney; histiocytes, including myointimal histiocytes in atherosclerosis; and mast cells, plasma cells, lymphocytes, and granulocytes.

Further clarification of expression in skeletal muscle showed variable staining, with strong staining of the motor end plates in a few samples. Staining varied from weak to strong in the anterior tibialis myocytes, the extensor digitorum longus, the gastrocnemius, the soleus, and in the vastus lateralis.

Murine tissue expression patterns of PDE11A demonstrated weak expression in testis in the germinal epithelium of the seminiferous tubules (spermatogonia, spermatocytes, spermatids, Leydig cells, and vascular smooth muscle). This expression is particularly prevalent in the spermatocytes.

B. Identification of PDE11A Agonists and Antagonists

One type of screen to identify PDE11A agonists and antagonists is conducted in vitro using native enzymes isolated from tissue, or using recombinant enzymes expressed in transfected host cells, for example, Sf9 insect cells (Fawcett, 2000), yeast cells (Loughney et al., U.S. Pat. No. 5,932,465), or COS-7 cells (Yuasa, 2000). Preferably, the PDE11A enzyme is human. Agents identified as PDE11A agonists or antagonists would likely produce similar effects on any other member of the PDE11 family.

PDE11A activity is measured, for example, as the rate of hydrolysis of an appropriate substrate, [$^3$H]cAMP or [$^3$H]cGMP. Agents that increase or decrease substrate hydrolysis are identified as PDE11A selective agonists (i.e., enhancers) or antagonists (i.e., inhibitors), respectively. This activity is measured, for example, by scintillation proximity assay (SPA)-based methods (Fawcett, 2000; Phillips et al., WO 00/40733, and Thompson et al., Biochem. 18: 5228, 1979 (as modified using product code TRKQ7090/7100, Amersham Int'l Ltd., Buckinghamshire, UK)). Briefly, samples containing the PDE11A enzyme are contacted with a cAMP or cGMP substrate (Sigma Chemical), a portion (e.g., ¼ to ½) of which is $^3$H labelled (Amersham). Reactions are conducted in, for example, microtiter plates (e.g., Microfluor® plates, Dynex Technologies, Chantilly, Va.), and are terminated by the addition of yttrium silicate SPA beads (Amersham) containing excess unlabeled cyclic nucleotide. After the beads are allowed to settle in the dark, plates are read by a microtiter plate reader (e.g., TopCount®, Packard, Meriden, Conn., USA).

PDE activity may also be assayed by detection of $^{32}$P-phosphate released from $^{32}$P-cAMP or $^{32}$P-cGMP (as described, for example, in Loughney et al., J. Biol. Chem. 271: 796–806, 1996, and Loughney, U.S. Pat. No. 5,932,465), or using antibodies to distinguish between the PDE substrates, cGMP or cAMP, and their hydrolyzed products (using, for example FlashPlate™ technology, NEN® Life Sciences Products, Boston, Mass.).

As an alternative to assaying PDE11A catalytic activity, agents can be identified as PDE11A agonists or antagonists if they indirectly modulate PDE11A catalytic activity, for example, via post-translational modification (e.g., phosphorylation), modulation of allosteric ligand binding (e.g., via the GAF domain (Fawcett, 2000)), or by binding to PDE11A themselves at either a catalytic or allosteric regulatory site. Agents that increase PDE11A catalytic activity via these mechanisms are identified as potential agonists; conversely, agents that decrease PDE11A catalytic activity via these mechanisms are potential PDE11A antagonists. Methods for determining PDE11A phosphorylation and allosteric ligand binding are described in the literature (see, e.g., McAllister-Lucas et al., J. Biol. Chem. 270: 30671–79, 1995, and Corbin et al., Eur. J. Biochem. 267: 2760–67, 2000).

Examples of agents that are screened include, but are not limited to, nucleic acids (e.g., DNA and RNA), carbohydrates, lipids, proteins, peptides, peptidomimetics, small molecules and other compounds. Agents can be selected individually for testing or as part of a library. These libraries are obtained using any of the numerous approaches in combinatorial library methods known in the art, and include: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (e.g., Lam, 1997, Anticancer Drug Des. 12:145; U.S. Pat. Nos. 5,738,996; and 5,807,683).

Examples of methods for the synthesis of molecular libraries can be found in the art, for example, in DeWitt et al., 1993, Proc. Natl. Acad. Sci. USA 90:6909, Erb et al., 1994, Proc. Natl. Acad. Sci. USA 91:11422, Zuckermann et al., 1994, J. Med. Chem. 37:2678, Cho et al., 1993, Science 261:1303, Carrell et al., 1994, Angew. Chem. Int. Ed. Engl. 33:2059, Carell et al., 1994, Angew. Chem. Int. Ed. Engl. 33:2061, and Gallop et al., 1994, J. Med. Chem. 37:1233.

Individual agents or libraries of agents may be presented in solution (e.g., Houghten, 1992, Bio/Techniques 13:412–421), or on beads (Lam, 1991, Nature 354:82–84), chips (Fodor, 1993, Nature 364:555–556), bacteria (U.S. Pat. No. 5,223,409), spores (U.S Pat. Nos. 5,571,698; 5,403, 484; and 5,223,409), plasmids (Cull et al., 1992, Proc. Natl. Acad. Sci. USA 89:1865–1869) or phage (Scott and Smith, 1990, Science 249:386–390; Devlin, 1990, Science 249:404–406; Cwirla et al., 1990, Proc. Natl. Acad. Sci. USA 87:6378–6382; and Felici, 1991, J. Mol. Biol. 222:301–310).

The effects of the test agents on PDE11A enzymatic kinetics (e.g., Vmax and Km) are determined in vitro, for example, by measuring hydrolysis with a fixed concentration of PDE11A enzyme, a range of substrate concentrations (e.g., 0.10–10 $\mu$M), and a time course ranging from, for example, 5–60 minutes. Agents that increase Vmax or decrease Km are identified as agonists. Agents that inhibit PDE11A activity decrease Vmax or increase Km and, preferably, have IC50 values in the nanomolar range. Such IC50 determinations involve assaying a fixed amount of purified recombinant or native PDE11A in the presence of various inhibitor concentrations and a low substrate concentration (e.g., 0.1–1.0 $\mu$M). Values for samples exposed to inhibitors are converted to percent activity of an uninhibited control (100%) and plotted against inhibitor concentration to find the concentration at which 50% inhibition occurs (IC50).

Preferably, the screen identifies PDE11A agonists and antagonists that are selective for a PDE11A enzyme. For example, a preferred agonist or antagonist is selective for PDE11A by at least 20 fold, more preferably, at least 30 fold, even more preferably, at least 50 fold, and, most preferably, at least 100 fold, as compared one or more PDEs from the group of PDEs 1–10. Preferred agonists and antagonists are selective for PDE11A as compared to one or more of PDE3, PDE4, PDE5, and/or PDE6.

For example, fold selectivity of an antagonist with respect to PDE11A as compared to another PDE is determined by dividing the IC50 value for the other PDE by the IC50 value for PDE11A. Fold selectivity comparisons may involve comparing PDE11A values to previously reported values for other PDEs, or testing the other PDE enzymes concurrently.

As an alternative to in vitro screens, compounds can be screened for PDE11A modulating effects in a cell-based, tissue-based, or whole animal based assay, using samples that express PDE11A endogenously or as a result of genetic engineering.

In addition to comparing such samples in the presence and absence of the agent, an additional negative control for such assays is testing the agent on an appropriately matched, genetically-modified, PDE11A–/– cell or tissue preparation or non-human mammal. Such samples can be used to verify whether or not any observed effect in PDE11A+/+ samples is mediated by PDE11A.

EXAMPLE

Identification of PDE11A Antagonists

Agents known to inhibit PDE5 were tested to determine whether they also modulated PDE11A activity according to the method described, e.g., in Fawcett, 2000 and in Phillips et al., WO 00/40733. The IC50 values of the agents for inhibiting PDE11A were compared to the IC50 values for inhibiting PDEs 5–10. PDE5 was isolated from human corpus cavernosum; PDE6 was isolated from bovine retina; and recombinant human PDEs 7–11 were produced by baculovirus expression in Sf9 cells (Fawcett, 2000, and Ballard et al., J. Urol. 159: 2164–71, 1998).

The agents tested included the following: sildenafil; UK-336,017 (IC351; (6R, 12aR)-6-(1,3-benzodioxol-5-yl)-2,3,6,7,12,12a-hexahydro-2-methyl-pyrazino[1',2':1,6] pyrido[3,4-b]indole-1,4-dione; CAS number: 171488–01–0; see, also, WO 9519978), UK-227,786 (E4021; 1-[4-[(1,3-benzodioxol-5-ylmethyl)amino]-6-chloro-2-quinazolinyl]-4-piperidinecarboxylic acid, monohydrochloride; CAS number: 150452-21-4; see, also, WO 9307124); and UK-235,187 (6-Chloro-2-(1H-imidazol-1-yl)-N-(phenylmethyl)-,4-quinazolinamine, dihydrochloride; CAS number: 157863-31-5; see, also, EP 579496).

Compounds were dissolved in DMSO (4 mM) and then diluted to 40 $\mu$M in buffer B (20 mM Tris-HCl, pH 7.4, 5 mM MgCl$_2$-hexahydrate, 2 mg/ml bovine serum albumin (BSA)) at 25° C. (all components are available from Sigma Chemicals, St. Louis, Mo.). This 40 $\mu$M solution was then serially diluted to prepare a half log dilution over at least 5 points. Samples of each range point (25 $\mu$l) were plated in duplicate in microtiter plates (Microfluor® plates, Dynex Technologies, Chantilly, Va.). Samples containing the PDE enzyme were then added to each well. Purified recombinant or native enzyme was diluted 1:500 in buffer B, and 25 $\mu$l of this dilution was added to each well. (This amount of enzyme was sufficient to ensure a linear reaction over time and concentration.) The enzyme and compound samples were then pre-incubated for 15 minutes at room temperature.

Substrate was added to each plate in 50 $\mu$l samples. Substrate consisted of 90 nM unlabelled cGMP (Sigma Chemicals), 48 nM $^3$H-GMP (Cat. No. RPNQO0150, Amersham International Ltd.) in buffer A (20 mM Tris-HCl, pH 7.4, 5 mM MgCl$_2$ hexahydrate) for a final cGMP concentration of 69 nM for PDE11A tests (the substrate concentration for the other PDEs tested was adjusted to be less that or equal to ⅓ Km). Following a 50 minute incubation at room temperature on a plate shaker set to ensure adequate mixing, the reaction was terminated by the addition of yttrium silicate SPA beads (Amersham) containing excess (3 mM) unlabeled cGMP. The plate was then shaken for 15 minutes to ensure even mixing and then beads were allowed to settle for 30 minutes. Plates were read by a microtiter plate reader (TopCount® plate reader, TopCount protocol 50, Packard, Meriden, Conn.).

The agents' IC50 values for inhibiting PDE11A were compared to those for inhibiting PDEs 5–10. As shown in Table 1 below, PDE5 inhibitors UK-336,017 (IC351), UK-227,786 (E4021), and UK-235,187 demonstrated selectivity for inhibiting PDE11A when compared to PDEs 7–10 (IC-351 was also selective for PDE11A over PDE6). By contrast, the PDE5 inhibitor sildenafil was not selective for PDE11A when compared to any of PDEs 5–10.

TABLE 1

| | IC50 | | | | | | |
|---|---|---|---|---|---|---|---|
| Compound | PDE5 | PDE6 | PDE7 | PDE8 | PDE9 | PDE10 | PDE11A |
| Sildenafil | 3.5 nM | 37.5 nM | 19.71 μM | 27.6 μM | 2.48 μM | 9.13 μM | 2.99 μM |
| UK-336,017 (IC351) | 6.74 nM | 1.5 μM | >100 μM | >100 μM | >100 μM | >100 μM | 37.0 nM |
| UK-227,786 (E4021) | 33.4 nM | 4.7 μM | >100 μM | >100 μM | >100 μM | >100 μM | 572 nM |
| UK-235,187 | 4.64 nM | 1.0 μM | >100 μM | >100 μM | >100 μM | >100 μM | 46.6 nM |

All results are the geometric mean of at least 3 determinations.

C. Phenotypic Characterization of PDE11A−/− and PDE11A+/− Mice

The genetically-modified PDE11A−/− and PDE11A+/− non-human mammals and animal cells of the invention that have reduced PDE11A polypeptide activity can be used to identify novel PDE11A-mediated biological functions based upon the appearance of any abnormal phenotypes, for example, as related to spermatogenesis, NO-mediated bladder relaxation, and vasodilation. Any abnormal phenotypes associated with decreased PDE11A activity establish a basis for identifying and developing PDE11A-targeted therapeutics for treating PDE11A-related diseases or conditions.

Example

PDE11A−/− Mice Demonstrate Reduced Spermatogenesis

Mice homozygous for the PDE gene disruption were compared to wild type mice to identify any abnormal phenotypes at the age of 6–8 weeks. Data was collected from physical examination, necropsy, histology, clinical chemistry, blood chemistry, body weight, organ weight, and the cytological evaluation of bone marrow. For these comparisons, six PDE−/− mice (3 males and 3 females), and four PDE11A+/+ wild-type mice (2 males and 2 females) were studied.

Histological studies revealed changes in the testes of male PDE11A−/− mice. These changes included reduced spermatogenesis, an increased sloughing of spermatogenic epithelial cells, a thinning of the spermatogenic epithelium, a decrease in average seminiferous tubule diameter, a degeneration of the epithelial cells lining the tubule, and increased sloughing of residual bodies. These PDE11A KO mice also demonstrated reduced epididymal sperm, increased multinucleate sperm precursors, and an increased appearance of cell fragments and proteinaceous debris. Other tissues examined were histologically normal. These other tissues included seminal vesicles, salivary gland, thymus gland, pituitary gland, thyroid gland, aorta, heart, liver, gallbladder, esophagus, caecum, colon, rectum, bones, joint tissue, spinal cord, bone marrow, trachea, larynx, skeletal muscle, sciatic nerve, tongue, mammary gland, ovary, uterus, cervix, ocular tissue, and Harderian glands. No consistent or significant differences between the PDE11A−/− mice and control mice were revealed in terms of blood chemistry analysis, organ weight, or body weight.

The abnormal phenotype observed in PDE11A−/− male mice indicates that PDE11A is normally involved in spermatogenesis. Therefore, inhibiting or enhancing PDE11A activity in a male mammal decreases or increases spermatogenesis, respectively. The role of PDE11A in spermatogenesis is further confirmed by PDE11A expression in the germinal epithelium of the seminiferous tubules, particularly in spermatocytes, of wild type mice.

Example

PDE11A−/− Mice Demonstrate Increased Capacitation in Spermatozoa

Sperm capacitation is a series of biochemical events that are triggered post-ejaculation leading to spermatozoa becoming 'switched on'. This enables sperm to undergo the acrosome reaction and ultimately fertilize an oocyte. Failure for spermatozoa to become capacitated may be an underlying cause of infertility, as could premature termination of capacitation via spontaneous acrosome loss. Pre-ejaculated spermatozoa are uncapacitated and become capacitated after ejaculation. Capacitation of sperm and the triggering of all the downstream consequences of this process are facilitated by the addition of a milieu of bioactive molecules that make up seminal fluid and are mixed with sperm at ejaculation. Whilst many of the constituents of this milieu remain to be elucidated, ATP is known to be an important element. It is well established that sperm physiology, in particular capacitation, is regulated by elevation of intra-spermatozoal cAMP. The phosphodiesterase sub-types that hydrolyze spermatozoal cAMP are uncharacterized. It has been suggested that premature capacitation of spermatozoa can negatively influence the fertilization ability (Thundathil, J., Gil, J., Januskauskas, A., et al. (1999). Relationship between the proportion of capacitated spermatozoa present in frozen-thawed bull semen and fertility with artificial insemination. Int. J. Andrology, 22, 366–373). Capacitated spermatozoa exhibit elevated metabolic rates, increased membrane fluidity and permeability, and if they do not reach the oocyte, they undergo spontaneous acrosome loss. Hence the lifespan of capacitated spermatozoa is limited (Thundathil et al, 1999). Prematurely capacitated sperm are less likely to survive until they reach the oocyte and site of fertilization, so it could be assumed.

Sperm suspensions were prepared by releasing the contents of mouse epididymides from 3 PDE11 knockout (KO) and 3 wild type (WT) mice into Tyrodes media. The extent of capacitation was measured using chlorotetracycline (CTC), 750 μM for 15 min at 37° C. The patterns of CTC fluorescence were observed under microscopy (Reference: Fraser, L. R. & Herod, J. E. Expression of capacitation-dependent changes in chlortetracycline fluorescence patterns in mouse spermatozoa requires a suitable glycolysable substrate. J. Reprod. Fert., 1990; 88(2): 611–21). Patterns reflected the functional state of spermatozoa, i.e. capacitated, uncapacitated and acrosome loss.

Figure 6:
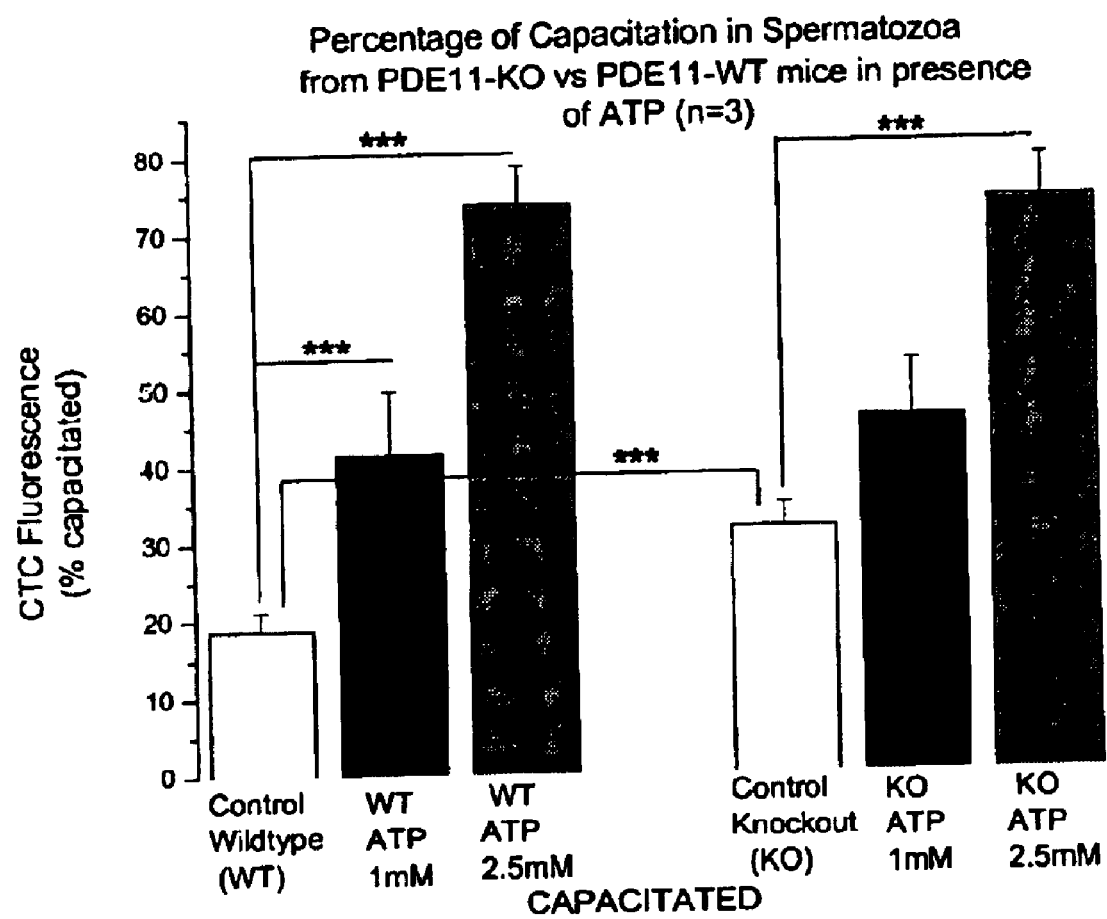
FIG. 6 shows the degree of capacitation in pre-ejaculated epididymal sperm suspensions obtained from PDE11 knockout (KO) and wild type (WT) mice. The extent of capacitation was measured using chlorotetracycline (CTC) and the degree of capacitation was assessed in control and adenosine-5'-triphosphate (ATP)-treated samples. All data is expressed as mean+s.e.mean, n=3, ***=P<0.001, Student's t-test). Control pre-ejaculated spermatozoa obtained from the PDE11 KO animals displayed a significantly higher extent of capacitation compared with sperm obtained from WT. mice (White bars, P<0.001, Student's t-test). ATP (2.5 mM) significantly increased the number of capacitated sperm in all murine spermatozoa samples after 1 hr incubation (Grey bars, P<0.001, Student's t-test) whereas only ATP (1.0 mM) significantly increased the number of capacitated sperm in spermatozoa obtained from PDE11 KO mice (Black bars, P<0.001, Student's t-test).

Baseline capacitation, of pre-ejaculated spermatozoa, was found to be significantly higher in PDE11 knockout mice compared with wild type mice (see FIG. 6). This data suggests that there is a significant proportion of premature capacitation in the sperm obtained from PDE11 knockout mice. This premature capacitation may impair the fertilization potential of these spermatozoa. The maximal extent of capacitation was similar between PDE11 knockout mice compared with wild type mice. In both samples, ATP significantly increased the number of capacitated murine spermatozoa after 1 hr incubation.

D. Genotypic Characterization of PDE11A−/− and PDE11A+/− Mice

The genetically-modified PDE11A−/− and PDE11A+/− non-human mammals and animal cells of the invention that have reduced PDE11A polypeptide activity can be used to identify novel PDE11A-mediated biological functions based upon the up- and/or down-regulation of certain genes, for example, as related to spermatogenesis, NO-mediated bladder relaxation, and vasodilation. Any abnormal gene expression associated with decreased PDE11A activity establishes a basis for identifying and developing PDE11A-targeted therapeutics for treating PDE11A-related diseases or conditions.

EXAMPLE

PDE11A−/− Mice Demonstrate Abnormal Gene Expression Compared to Wild-type Mice

RNA Extraction

Tissue frozen in liquid nitrogen (from the testis of PDE11A−/− knock-out (KO) mice and wild-type (WT) mice) was pulverized using a dismembrator (B. Braun Biotech International) and lysed in Buffer RLT (Qiagen, Germany). The solution was homogenized using a Qiashredder (Qiagen) and the RNA extracted using RNeasy columns (Qiagen), following the manufacturer's protocol.

Affymetrix Gene Expression Analysis

Double stranded cDNA was generated from 10 μg total RNA using Superscript Choice kit (Invitrogen (Life Technologies) Limited, Scotland, UK) with a T7-polyT primer. Approximately 1 μg cDNA was used to generate biotinylated cRNA by in vitro transcription using Bioarray High Yield RNA Transcript Labeling Kit (Enzo, USA). 10 μg fragmented cRNA was hybridized in 100 mM MES, 1M Na$^+$, 20 mM EDTA, 0.01% Tween 20, 0.1 mg/ml herring sperm DNA, 0.5 mg/ml acetylated BSA plus 50 pM control oligonucleotide and eukaryotic hybridization controls to Murine Genome U74A arrays (MGU74A arrays—Catalogue Nos.: 900321 or 900322; Affymetrix, Calif., USA) at 45° C. for 16 hours. Arrays were washed using Affymetrix protocols in non-stringent buffer (6×SSPE, 0.01% Tween 20, 0.005% antifoam) at 25° C. and stringent wash buffer (100 mM MES, 0.1 M Na$^+$, 0.01% Tween) at 50° C. and stained with streptavidin phycoerythrin (10 μg/ml) including an antibody amplification step. Arrays were scanned using a laser confocal scanner to generate fluorescence intensities. The data were processed using Microarray Analysis Suite version 4.0 (Affymetrix). Approximately 2,600 probe sets identified by Affymetrix as non-functional were masked out of the analysis. The data were scaled to a target intensity of 300.

Data Analysis of the n=4 Data Set

The data was subsequently analyzed using Spotfire Array Explorer 3.0 software (see, for example, U.S. Pat. No. 6,014,661). Genes were initially selected based on expression profiles which were "high in WT/low in KO" (i.e. down-regulated by PDE11 ablation) or "low in WT/high in KO" (i.e. up-regulated by PDE11 ablation). The 1000 genes so selected were then triaged on the basis of expression level and fold change (at least 2 fold between WT and KO)—this removed the majority of the genes. Expressed sequence tag (EST) clusters (function unknown at present) were then also removed. This left 108 genes, either down- or up-regulated which have a known function. Each of these genes were then researched in Medline for an involvement in, inter alia, testis function, cAMP and/or cGMP-mediated signal transduction. Of the 72 down-regulated genes in the KO mice, 15 have some known link to testis. Of the 35 up-regulated genes, 6 have some known link to testis.

Summary of data analysis of genes down-regulated in PDE11 KO testis 500 genes were identified which show similarity to an expression profile of high in WT/low in KO.

Of these, 199 genes were not expressed at significant levels in either WT or KO for the results to be meaningful and were disregarded.

Of the 301 genes left, 170 genes showed less than a 2-fold differential expression between WT and KO. Although statistically all of these genes were significantly differentially expressed to at least a significance of P=0.05, for the purposes of the present analysis they were excluded.

Of the remaining 131 genes, 59 genes were derived from mouse EST clusters and have no identifiable function at present.

Of the remaining 72 genes, 43 genes had no discernible role in, inter alia, testis function based on searches of the literature.

Of the remaining 29 genes, 12 genes were excluded for other reasons.

2 further genes were known to be involved in xenobiotic metabolism.

This left 15 genes (see below), which have varying links to testicular function and are significantly down-regulated in the PDE11 KO testis.

Summary of data analysis of genes up-regulated in PDE11 KO testis 500 genes were identified which show similarity to an expression profile of low in WT/high in KO.

Of these, 269 genes were not expressed at significant levels in either WT or KO for the results to be meaningful and were disregarded.

Of the 231 genes left, 161 genes showed less than a 2-fold differential expression between WT and KO. Although statistically all of these genes were significantly differentially expressed to at least a significance of P=0.05, for the purposes of the present analysis they were excluded.

Of the remaining 70 genes, 35 genes were derived from mouse EST clusters and have no identifiable function at present.

Of the remaining 35 genes, 28 genes had no discernible role in, inter alia, testis function based on searches of the literature.

1 gene was known to be involved in xenobiotic metabolism.

This left 6 genes (see below), which have varying links to testicular function and are significantly up-regulated in the PDE11 KO testis.

Gene Expression

Figure 4:
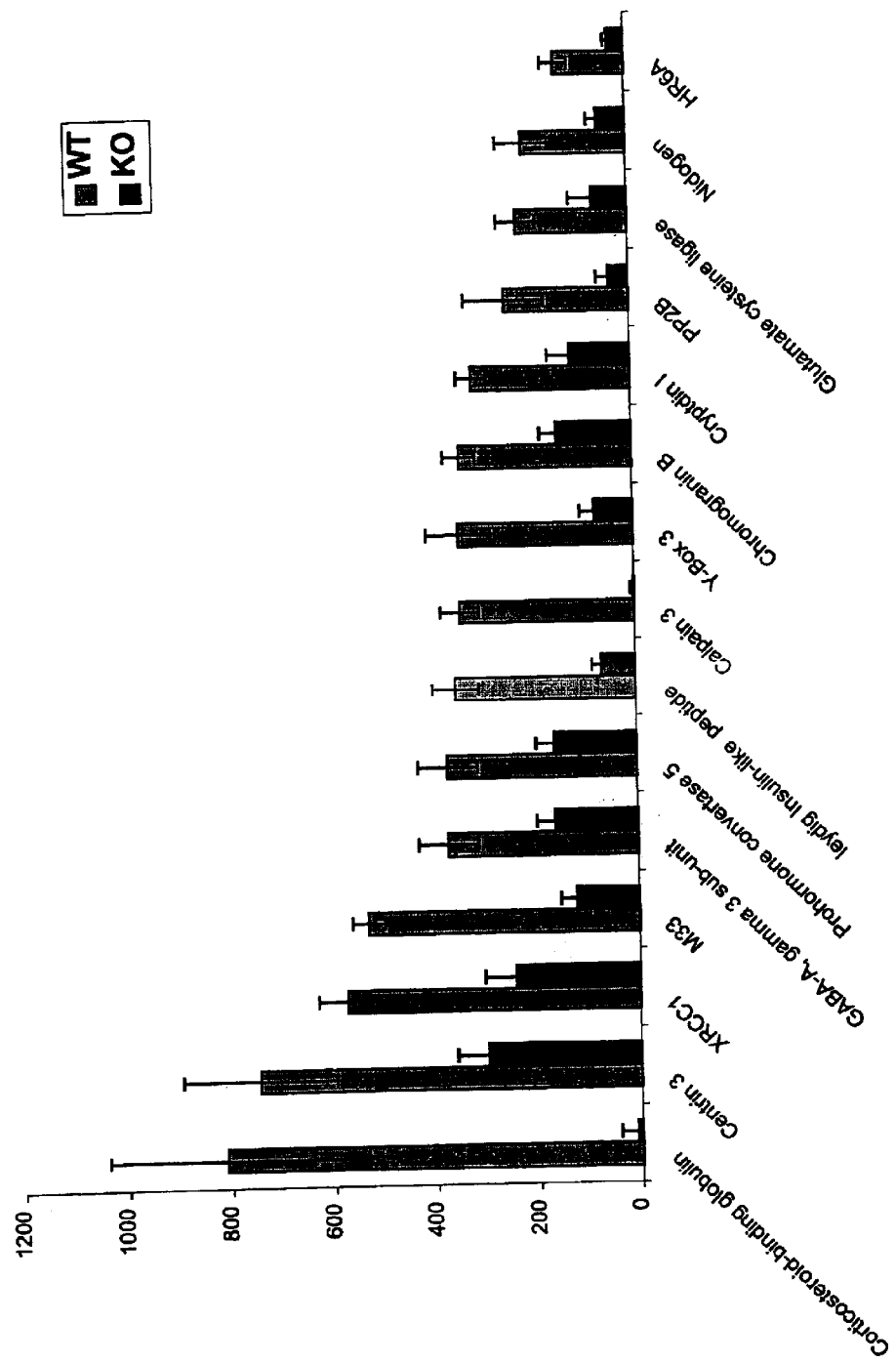
FIG. 4 shows a histogram illustrating the fifteen genes which show down-regulation of expression in the testis of PDE11 knockout (KO) mice (n=4) compared to wild type (WT) animals (n=4). The histogram bars are average values and error bars are +/−1 standard deviation.
Figure 5:
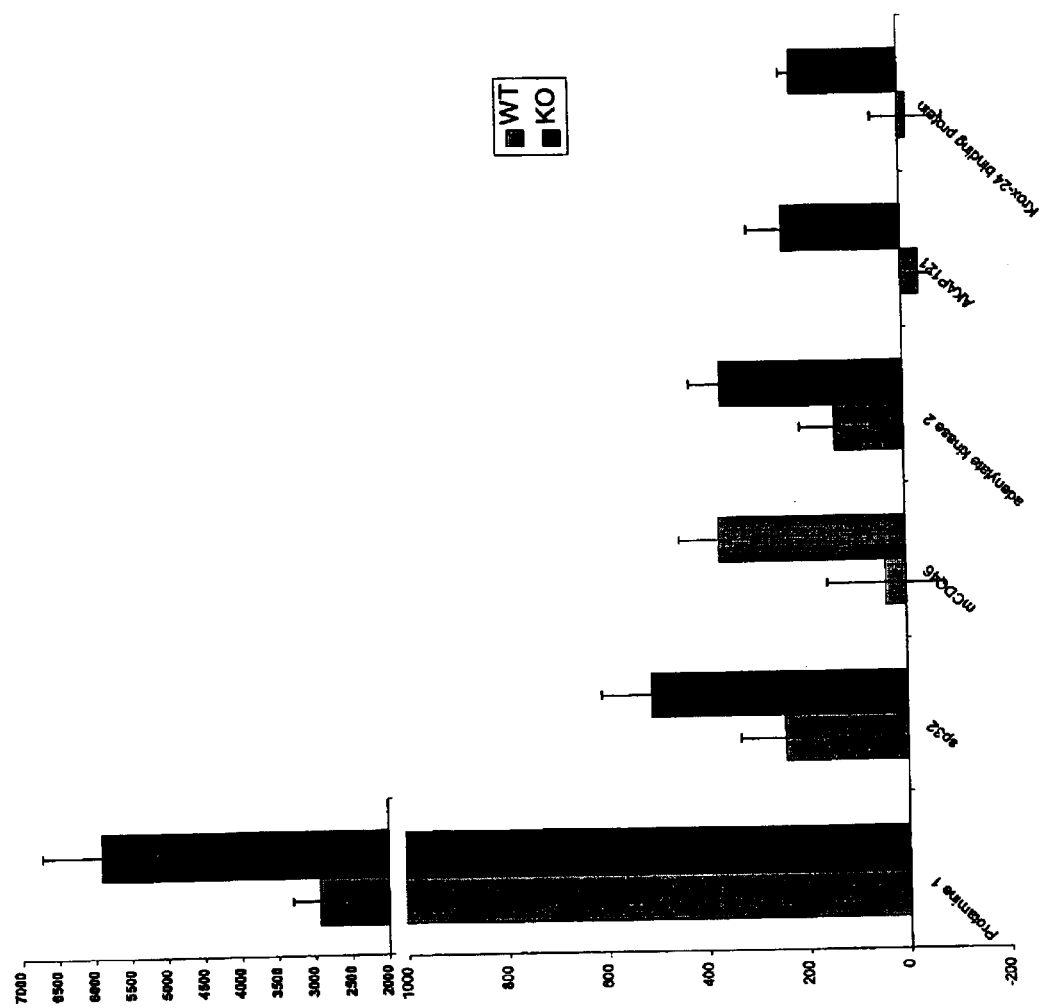
FIG. 5 shows a histogram illustrating the six genes which show up-regulation of expression in the testis of PDE11 knockout (KO) mice (n=4) compared to wild type (WT) animals (n=4). The histogram bars are average values and error bars are +/−1 standard deviation.

The microarray data showed fifteen genes that were down-regulated in the testis of PDE11 knock-out mice (n=4) compared to wild type animals (n=4) (see FIG. 4) and six genes that were up-regulated in the testis of PDE11 knock-out mice (n=4) compared to wild type animals (n=4) (see FIG. 5).

15 Down-regulated Genes

1. Corticosteroid binding globulin is known to be involved in the transport of steroids (e.g. testosterone) and it is related to Serpins. Primary expression is in the liver, but also expressed in testis (Proc. Natl. Acad. Sci. USA 84:5153). Down regulation of this gene will affect transport of the testosterone secreted by Leydig cells. It could have down-stream affects on spermatid viability or secondary sexual characteristics.
2. Centrin 3 is an essential protein involved in centromere formation and cell cycle progression. Down regulation of Centrin might affect mitotic turnover and therefore, reduce the numbers of spermatids produced.
3. XRCC1 is involved in DNA strand-break repair, homologous recombination, and sister chromatid exchange. Expression is known not to change over time in mice. Therefore, down regulation of XRCC1 may cause incorrect repair of DNA during mitosis (Brain Res. 869:105).
4. Chromobox M33 is a transcription factor and is related to Polycomb. Down regulation of this protein could mimic the sex reversal phenotype seen in the KO mouse.
5. GABA-A, gamma 3 sub-unit is an important structural component of the GABA-A receptor. GABA is known to be required for the acrosome reaction. Down regulation of this sub-unit may cause inefficient signalling via the GABA-A receptor which may impair the acrosome reaction.
6. Prohormone convertase 5 is thought to activate MIS. Down regulation of this protease could cause developmental abnormalities associated with improper mullerian duct regression.
7. Leydig Insulin-like peptide is a Relaxin-like factor involved in gubernaculum development. Down regulation of this gene could mimic aspects of the Ley-L KO mouse e.g. cryptochordism of the testis.
8. Calpain 3 is involved in the acrosome reaction. Other calpains are not down regulated. Down regulation of Calpain 3 might affect the acrosome reaction.
9. Y-Box 3 is involved in transcription. Other Y-Box proteins are not down regulated. As it is suspected to be an import transcription factor in testis, down regulation could have multiple affects on testicular physiology.
10. Chromogranin B is Involved in secretion from endocrine tissues. Down regulation of this protein might disrupt secretory pathways of the Leydig cells and thereby causing alterations in the interstitial microenvironment.
11. Cryptdin I is important for defense against infective bacteria. Cryptdins have been shown to be involved in bacterial defense in the testis. Therefore, reduced cryptidin expression could make testis susceptible to infection.
12. PP2B is a phosphatase known to be involved in the Calmodulin-mediated calcium signalling pathway which is key for spermatogenesis. Down regulation of this protein might cause disturbance to calcium signalling and affect efficient spermatogenesis.
13. Glutamate cysteine ligase is involved in the Gamma glutamyl cycle. As this cycle is known to be essential for spermatogenesis, down regulation could inhibit this process.
14. Nidogen is involved in adhesion of the peritubular cells to extracellular matrix. Down regulation of this gene could cause instability in the peritubular cells and improper spermiation and migration.
15. HR6A is involved in Ubiquitin conjugation. Down regulation of this protein could mimic the compromised spermatogenesis consistent with the phenotype seen in the KO mouse.

6 Up-regulated Genes

1. Protamine 1 is a histone like protein which is specific to testis. Changes in protamine 1 regulation is known to cause incorrect condensation of the spermatid nucleus.
2. sp32 is a proacrosin-binding factor. It accelerates activation of proacrosin which could be deleterious to fertilization efficiency.
3. mCDC46 is a DNA replication-licensing factor which is essential for DNA replication. Up regulation could reflect deleterious changes in the testis.
4. Adenylate kinase 2 is important for nucleotide regulation. Up regulation could be a response to elevated cAMP levels.
5. AKAP121 is a kinase anchor protein. It is known to be regulated by cAMP and hormones. Up regulation could reflect deleterious changes in testicular microenvironment.
6. Krox-24 binding protein binds with Zinc-finger transcription factor which activates EGR. Increased expression may contribute to the infertility of the knock-out mice.

E. Identification of PDE11A Function Using PDE11A Agonists and Antagonists

Compounds identified as modulators of PDE11A, more preferably, compounds that are identified as selective PDE11A modulators, can be administered to cells or tissue preparations that express PDE11A, or to whole animals, to identify PDE11A function based upon changes that occur in response to compound administration.

For example, given PDE11A expression in bladder urothelium, it is a candidate as a regulator of nitric oxide (NO)-mediated inhibition of bladder and bladder nerve fiber excitability. This NO-mediated effect is described, e.g., in Ozawa et al., J. Urol. 162: 2211, 1999, Pandita et al., J. Urol. 545–550, 2000, and Burnett et al., Nat. Med. 3: 571–74, 1997. To characterize the role of PDE11A in bladder contractility, the effects of a PDE11A antagonist can be studied in a model of oxyhemoglobin-induced (Pandita, supra) or cyclophosphamide-induced (Ozawa, supra), bladder hyperactivity. Experimental animals (e.g., rats) are administered oxyhemoglobin (intravesically, Sigma Chemical) or cyclophosphamide (intraperitoneally) in combination with a PDE11A antagonist dissolved, e.g., in DMSO and diluted by an appropriate buffer. The PDE11A antagonist is administered by an appropriate route (e.g., intravesically, intraperitoneally, or intravenously).

PDE11A is identified as playing a role in regulating NO-mediated inhibition of bladder and bladder nerve fiber excitability in test animals if a PDE11A antagonist causes a decrease in neuronal firing in afferent neurons innervating the bladder, a decrease in bladder contraction frequency, a decrease in micturition pressure, and/or a decrease basal pressure, as compared to control animals not administered the antagonist. The measures of bladder function are made according to standard methods described in the literature (e.g. Pandita (supra), and Ozawa (supra)). As an additional control to confirm that the observed effect was mediated by inhibiting PDE11A, appropriately matched, genetically-modified non-human mammals containing a disrupted PDE11A gene (preferably, PDE11A−/−) may be tested.

When testing the effect of an agent that modulates PDE11A activity or expression, it is preferred to use tissue or cell samples that express human PDE11A, such as those derived from human cell lines or from a primary human tissue preparation. Alternatively, such tissue or cell samples may be obtained from a PDE11A humanized non-human mammal or animal cell. Similarly, one preferred test animal for PDE11A functional studies is a genetically-modified PDE11A humanized mammal.

F. Therapeutic Applications

Agents identified as modulating PDE11A activity can be used for therapeutic purposes. Preferably, the agent is selective for PDE11A with respect to at least one other PDE (e.g. UK-336,017 (IC351), UK-227,786 (E4021), and UK-235, 187 are selective for PDE11A, as compared to PDEs 7–10), more preferably, the agent is selective for PDE11A with respect to at least one of PDE3, PDE4, PDE5, and/or PDE6 (e.g., UK-336,017 (IC-351 is selective for PDE1IA as compared to PDE6).

Exemplary therapeutic applications are as follows: administering the agent to modulate spermatogenesis for use as either a male contraceptive (by decreasing PDE11A activity and decreasing spermatogenesis) or to increase male fertility (by stimulating PDE11A activity and stimulating spermatogenesis) or for modulating skeletal muscle metabolism or contractility; administering the agent to decrease PDE11A activity for the treatment of a hyperexcitable or overactive bladder, cardiac insufficiency, hypertension, atherosclerosis, hyperprolactinemia, or conditions or disorders that improve as a result of increased growth hormone secretion. Agents that modulate PDE11A activity may be administered by any appropriate route. For example, administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

PDE11A is expressed in cardiac myocytes, the endothelial cell lining and the medial smooth muscle cells of the cardiac vasculature. Modulation of cAMP levels in cardiac myocytes is well documented as having a clear effect on cardiac contractility via downstream modulation of ionic currents, as exemplified by inhibition of PDE3 (e.g., using amrinone and milrinone) leading to a positive inotropic response via increased cAMP levels (Fischer et al., Drugs 44: 928–45, 1992). Cyclic GMP has also been shown to be involved in modulating cardiac contractility. For example, in rat myocytes, moderate increases in cGMP in response to nitric oxide (NO) donors were associated with an improved contractile response via a cAMP-dependent pathway, whereas large cGMP increases reduced contractile responses (Kojda et al., Circ. Res. 78: 91–101, 1996). Furthermore, elevation of cGMP due to exposure to a cytokine (via inducible nitric oxide synthase), a C-type natriuretic peptide (Joe et al., J. Mol. Cell. Cardiol. 30: 303–15, 1998; Brusq et al., Br. J. Pharmacol. 128: 206–12, 1999), or due to pharmacological manipulation (Weiss et al., Can. J. Physiol. Pharmacol. 77: 422–31, 1999), have also been reported to either enhance relaxation or decrease the cardiac contractility. Therefore, modulators of PDE11A can play a role in either positively or negatively modulating cardiac myocyte contractility.

In addition to their roles in cardiac myocytes, cGMP and cAMP are also well documented as having key regulatory roles in vascular smooth muscle cell (VSMC) function. For example, elevation of cGMP levels via the NO-cGMP signalling pathway can mediate vasorelaxation (Ignarro et al., J. Cardiovasc. Pharmacol. 34: 879–86, 1999). Similarly, elevated cAMP, e.g., following beta-agonist stimulation, can mediate VSMC relaxation by various intracellular mechanisms that ultimately cause a decrease in intracellular $Ca^{++}$ levels (Wilson and Warren, Br. J. Pharmacol. 110: 633–38, 1993). Cyclic AMP and cGMP have also been reported to affect VSMC proliferation, (Indolfi et al., Nat. Med. 3: 775–79, 1997; Kariya et al., Atherosclerosis 80: 143–47, 1989; Fukumoto et al., Circ. Res. 85: 985–91, 1999; Koyama et al., J. Cell. Physiol. 186: 1–10, 2001). Therefore, modulation of either cGMP or cAMP via modulating PDE11A activity can affect vascular tone (and hence blood pressure) as well as VSMC proliferation.

PDE11A is expressed in the myocytes of a range of muscle types but to varying degrees and in varying proportions of cells (i.e., in a mosaic pattern). A range of skeletal muscle functions, such as metabolism and force generation (i.e., excitation-contraction coupling), are reported to be modulated by both cGMP and cAMP. For example, glucose uptake, glycolysis, mitochondrial oxygen consumption and creatine kinase activity are reported to be NO-sensitive, via the NO-cGMP pathway. The increase in cGMP results in an increase in 'fuel' oxidation (Young & Leighton, FEBS Lett. 424: 79–83, 1998; Stamler and Meissner, Physiol. Rev. 81: 209–37, 2001). NO can also modulate skeletal muscle contraction, inhibiting force output by altering excitation-contraction coupling (Reid, Acta. Physiol. Scand. 162: 401–09, 1998). Conversely, cAMP has been shown to be important for excitation-contraction coupling, and hence force generation (Grossman et al., J. Card. Fail. 2: (4 Suppl.): S105–11, 1996; Bishop et al., Ann. N.Y. Acad. Sci 853: 209–219, 1998). Therefore, modulation of either cGMP or cAMP via PDE11A inhibition, for example, may affect muscle metabolism (fuel consumption) and/or contractility (force generation), and, therefore, such modulation can play a role in muscle fatigue and performance.

PDE11A is expressed in many cells of the germinal epithelium within the seminiferous tubules of the testis, i.e., spermatogonia, spermatocytes, and spermatids, as well as the interstitial (Leydig) cells. In addition to the reduced spermatogenesis observed in male PDE11A–/– mice at 6–8 weeks of age, several other lines of evidence indicate that PDE11A plays an important role in spermatogenesis via modulating cAMP. For example, components of the cAMP signalling pathways are known to be expressed in germ cells, i.e., cAMP-dependent protein kinase (PKA) (Lonnerberg et al., Biol. Reprod. 46: 1057–68, 1992), the PKA anchoring protein AKAP84 (Lin et al., J. Biol. Chem. 270: 27804–11, 1995) and the cAMP response element modulator CREM (Nantel et al., Nature 380: 159–62, 1996). The latter, CREM, is a transcription factor that acts as a down-regulator of cAMP-induced gene transcription (Foulkes et al., Cell 64: 739–49, 1996), and is expressed at high levels beginning in pachytene spermatocytes. Mice that are null for CREM, via gene knockout, produce no mature sperm and are sterile (Nantel et al., supra) presumably due to the ablation of the inhibition of cAMP-induced gene transcription. Consequently, enhancement of cAMP levels in spermatocytes via PDE11A inhibition, for example, may over-ride the down-regulation of cAMP-Induced gene transcription by CREM and lead to suppression of spermatogenesis.

In addition to spermatogenesis, cAMP has also been reported to be an important messenger in the maintenance of motility in mature sperm (Chaudhry et al., Cell Motil. Cytoskeleton 32: 65–79, 1995). Furthermore, it also has a key role in eliciting the signaling events leading to capacitation and the acrosome reaction in sperm (Duncan & Fraser, J. Reprod. Fertil. 97: 287–99, 1993; Aitken et al., J. Cell Sci. 111: 645–656, 1998; Adeoya-Osiguwa & Fraser, Mol. Reprod. Dev. 57: 384–92, 2000); the latter being important to sperm activation and fertility. Consequently, perturbation of cAMP levels in spermatocytes, spermatids and spermatozoa via PDE11A inhibition, for example, can suppress spermatogenesis, but enhance sperm motility and/or sperm activation upon ejaculation.

The interstitial (Leydig) cells produce testosterone, which is necessary for spermatogenesis, development and maintenance of accessory glands of the male reproductive system, e.g., seminal vesicles, and the secondary male sex characteristics. Testosterone biosynthesis in Leydig cells is primarily regulated by pituitary gonadotrophin luteinising hormone (LH) through activation of a cAMP-PKA-dependent pathway (Cooke, Mol. Cell. Endocrinol. 151: 25–35, 1999). The regulation of testosterone biosynthesis can also involve several other paracrine and autocrine factors, e.g., insulin-like growth factor I (Rouiller-Fabre et al., Endocrinology 139: 2926–34, 1998) and TNF alpha (Xiong & Hales, Endocrinology 132: 2438–44, 1990), again acting via cAMP. Furthermore, cGMP has been reported to be involved in the modulation of testosterone secretion in Leydig cells. For example, NO biphasically modulates testosterone production in cultured rat Leydig cells; low dose NO-donors increase cGMP levels and testosterone secretion (Valenti et al., Int. J. Androl. 22: 336–41, 1999). Therefore, modulation of cAMP and/or cGMP via modulating PDE11A in Leydig cells can either positively or negatively affect testosterone production, spermatogenesis, and/or testis development.

PDE11A is expressed in the acidophils of the anterior pituitary, i.e., somatotrophs and lactotrophs. The presence of PDE11A in acidophils indicates that PDE11A plays a role in modulating the secretion of prolactin and/or growth hormone, which are secreted from the lactotrophs and somatotrophs respectively. For example, NO has been demonstrated to inhibit prolactin secretion via elevation of cGMP (Duvilanski et al., Proc. Natl. Acad. Sci. USA 92: 170–74, 1995). Therefore, the elevation of cGMP levels in lactotrophs produced via PDE11A inhibition, for example, can be useful to reduce secretion of prolactin for treating disorders related to hyperprolactinemia. Prolactin, in addition to its well-established role in lactation, has a diverse range of activities, which include effects on luteal function, steroidogenesis, immuno-regulation, growth, testis development and spermatogenesis (Bole-Feysot et al., Endocr. Rev. 19: 225–68, 1998). Mice that are null for the prolactin receptor exhibit infertility, lack normal mammary development and depressed maternal behavior (females), delayed fertility (males), reduced bone formation and a slight reduction in body weight (Kelly et al., Front. Neuroendocrinol. 22: 140–45, 2001). These effects could be manifest in response to reduced or ablated prolactin secretion. Accordingly, a PDE11A agonist can be used to decrease the levels of cAMP and cGMP in anterior pituitary lactotrophs and increase prolactin secretion.

Cyclic AMP elevation in somatotrophs, in response to growth hormone-releasing hormone (GHRH) stimulation, results in the release of growth hormone (GH) from secretory granules (Mayo et al., Recent Prog. Horm. Res. 50: 35–73, 1995), and hence PDE11A inhibition in anterior pituitary somatotrophs, for example, can enhance this release. This enhancement of GH release can be important, for example, for bone growth and maintenance (Murray & Shalet, Expert Opin. Pharmacother. 1: 975–90, 2000), and for the treatment of frailty associated with ageing, osteoporosis, morbid obesity, cardiac failure, major thermal injury and various acute and chronic catabolic conditions.

When administering therapeutic formulations comprising an agent that modulates PDE11A activity, the formulations may be in the form of liquid solutions or suspensions, in the form of tablets or capsules, or in the form of powders, nasal drops, or aerosols. Methods well known in the art for making formulations are found, for example, in Remington's Pharmaceutical Sciences (ed. Gennaro, Mack Publishing Co., Easton, Pa., $18^{th}$ ed., 1990).

What is claimed is:

1. A transgenic mouse, wherein said mouse is homozygous for disruption of the phosphodiesterase 11A (PDE11A) gene wherein said mouse exhibits nondetectable PDE11A activity and wherein a male mouse containing said homozygous disruption demonstrates reduced spermatogenesis or increased capacitation in spermatozoa.

2. A transgenic cell, derived from the transgenic mouse of claim 1.

3. The cell of claim 2, wherein said cell is an embryonic stem (ES) cell.

* * * * *